United States Patent
Gough et al.

(10) Patent No.: US 12,336,973 B2
(45) Date of Patent: Jun. 24, 2025

(54) CANCER THERAPEUTIC COMPOSITIONS AND METHODS TARGETING DNASE1L3

(71) Applicants: Providence Health & Services—Oregon, Portland, OR (US); Oregon Health & Science University, Portland, OR (US)

(72) Inventors: Michael Gough, Portland, OR (US); Marka Crittenden, Portland, OR (US); Tiffany Blair, Portland, OR (US)

(73) Assignees: Providence Health & Services—Oregon, Portland, OR (US); Oregon Health & Science University, Portland, OR (US)

(*) Notice: Subject to any disclaimer, the term of this patent is extended or adjusted under 35 U.S.C. 154(b) by 0 days.

(21) Appl. No.: 18/044,066

(22) PCT Filed: Sep. 24, 2021

(86) PCT No.: PCT/US2021/051942
§ 371 (c)(1),
(2) Date: Mar. 3, 2023

(87) PCT Pub. No.: WO2022/067032
PCT Pub. Date: Mar. 31, 2022

(65) Prior Publication Data
US 2023/0241015 A1    Aug. 3, 2023

Related U.S. Application Data
(60) Provisional application No. 63/083,645, filed on Sep. 25, 2020.

(51) Int. Cl.
| | |
|---|---|
| *A61K 31/198* | (2006.01) |
| *A61K 31/53* | (2006.01) |
| *A61K 31/7105* | (2006.01) |
| *A61K 31/727* | (2006.01) |
| *A61P 35/00* | (2006.01) |
| *C12N 15/113* | (2010.01) |

(52) U.S. Cl.
CPC ............ *A61K 31/198* (2013.01); *A61K 31/53* (2013.01); *A61K 31/7105* (2013.01); *A61K 31/727* (2013.01); *A61P 35/00* (2018.01); *C12N 15/1137* (2013.01)

(58) Field of Classification Search
CPC .. A61K 31/198; A61K 31/53; A61K 31/7105; A61K 31/727; A61K 31/255; A61K 31/713; A61K 45/06; A61P 35/00; C12N 15/1137; C12N 2310/14; C12Y 301/21; A61N 2005/1098
See application file for complete search history.

(56) References Cited

U.S. PATENT DOCUMENTS

| 8,841,416 B2 | 9/2014 | Ledbetter et al. |
| 2011/0098189 A1 | 4/2011 | Lapointe et al. |

FOREIGN PATENT DOCUMENTS

| JP | 2006036711 A | 2/2006 |

OTHER PUBLICATIONS

Deng. OncoTargets and Therapy 2021:14 2003-2017 (Year: 2021).*
Shi. Front. Immunol. 2017; 8: 522 (Year: 2017).*
Ma. Cell Adh Migr, 2020; 14(1): 118-128 (Year: 2020).*
Naipirei. Biochem J, Jul. 2005l 389 Pt. 2: 335-364 (Year: 2005).*
Keyel. Development Biology, vol. 429, Iss. I, 2017 (Year: 2017).*
Li et al. JCI Insight. 2023;8 (17): e168161 (Year: 2023).*
Shi, Front. Immunol. 8:52, 2017 (Year: 2017).*
Baird et al., "Radiation therapy combined with novel STING-targeting oligonucleotides results in regression of established tumors," *Cancer Res*, vol. 76, No. 1, pp. 50-61, 2016.
Baird et al., "Stimulating innate immunity to enhance radiation therapy-induced tumor control," *Int J Radiat Oncol Biol Phys.*, vol. 99, No. 2, pp. 362-373, 2017.
Blair et al., "Dendritic Cell Maturation Defines Immunological Responsiveness of Tumors to Radiation Therapy," *J Immunol*, vol. 204, No. 12, pp. 3416-3424, 2020.
Carozza et al., "Extracellular cGAMP is a cancer-cell-produced immunotransmitter involved in radiation-induced anticancer immunity," *Nature Cancer*, vol. 1, pp. 184-196, 2020.
Deng et al. "DNASE1 L3 as a Prognostic Biomarker Associated with Immune Cell Infiltration in Cancer," *OncoTargets and Therapy*, vol. 14, pp. 2003-2007, 2021.
Hayakawa et al. "Cladribine Enhances Apoptotic Cell Death in Lung Carcinoma Cells Over-Expressing DNase γ," *Biological and Pharmaceutical Bulletin*, vol. 34, No. 7, pp. 1001-1004, 2011.
International Search Report and Written Opinion dated Jan. 7, 2022, for PCT/US2021/051942 (9 pages).

(Continued)

*Primary Examiner* — Jeffrey H Murray
*Assistant Examiner* — Luisalberto Gonzalez
(74) *Attorney, Agent, or Firm* — Klarquist Sparkman, LLP

(57) ABSTRACT

Methods for treating a subject with cancer, including administering to the subject an effective amount of an inhibitor of DNAse1L3 and an effective amount of radiation therapy are provided. In some examples, the methods involve enhancing or inducing response of tumor-associated immune cells in the subject, including administering to the subject an effective amount of radiation therapy, and administering to the subject an effective amount of an inhibitor of DNAse1L3, thereby enhancing or inducing the response of tumor-associated immune cells in the subject. In some examples, the tumor-associated immune cells comprise dendritic cells or macrophages.

14 Claims, 8 Drawing Sheets
Specification includes a Sequence Listing.

(56) References Cited

OTHER PUBLICATIONS

Le et al., "Localized irradiation of tumors prior to synthetic dsRNA therapy enhanced the resultant anti-tumor activity," Radiother Oncol. vol. 90, No. 2, pp. 273-279, 2009.
Seidl et al. "$^{213}$Bi-induced death of $HSC_{45}$-M2 gastric cancer cells is characterized by G2 arrest and up-regulation of genes known to prevent apoptosis but induce necrosis and mitotic catastrophe," *Molecular Cancer Therapeutics*, vol. 6, No. 8, pp. 2346-2359, 2007.
Sisirak et al., "Digestion of Chromatin in Apoptotic Cell Microparticles Prevents Autoimmunity," *Cell*, vol. 166, No. 1, pp. 88-101, 2016.
Vanpouille-Box et al., "DNA exonuclease Trex1 regulates radiotherapy-induced tumour immunogenicity," *Nature communications*, vol. 8, No. 1, p. 15618 (1-15), 2017.
Wilber et al., "Dnase1l3 deficiency in lupus-prone MRL and NZB/W F1 mice," *Clin. Exp. Immunol*, vol. 134, pp. 46-52, 2003.
Yoshida et al., "Toll-like receptor 3 signal augments radiation-induced tumor growth retardation in a murine model," *Cancer Science*, vol. 109, pp. 956-965, 2018.
Yamada et al., "DR396, an apoptotic DNase γ inhibitor, attenuates high mobility group box 1 release from apoptotic cells," *Bioorganic & Medicinal Chemistry* 19:168-171, 2011.

\* cited by examiner

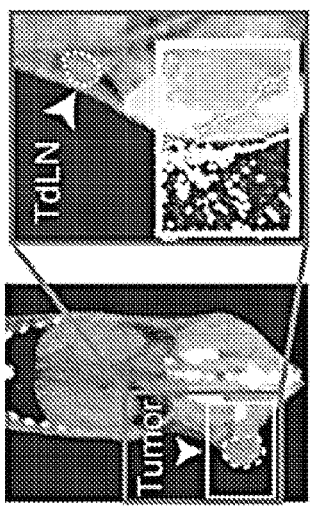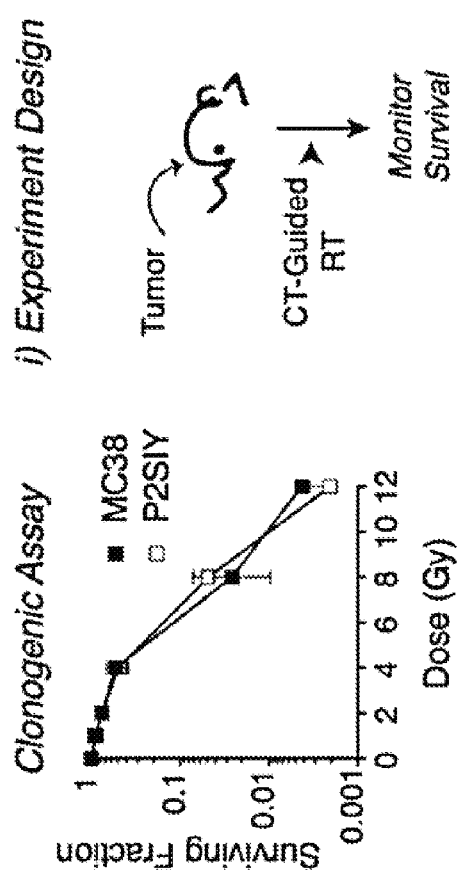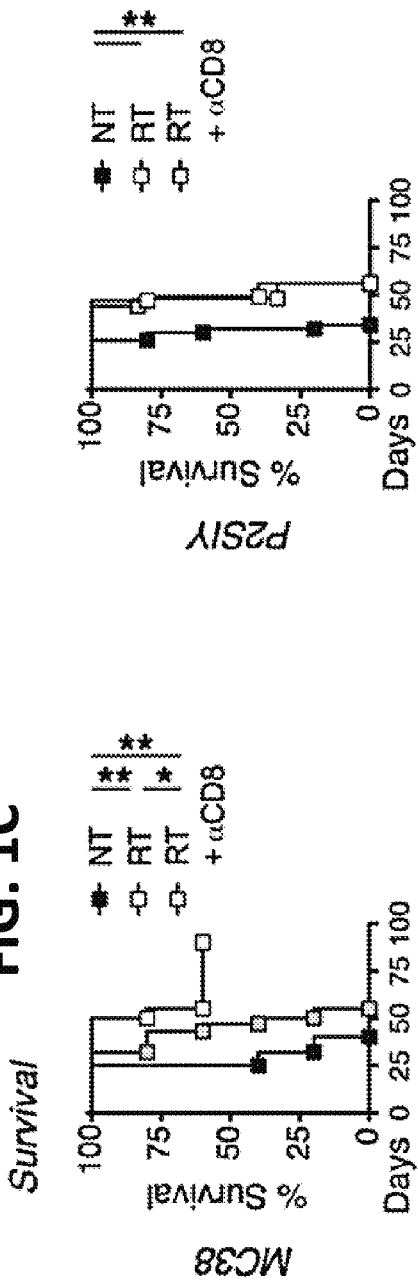

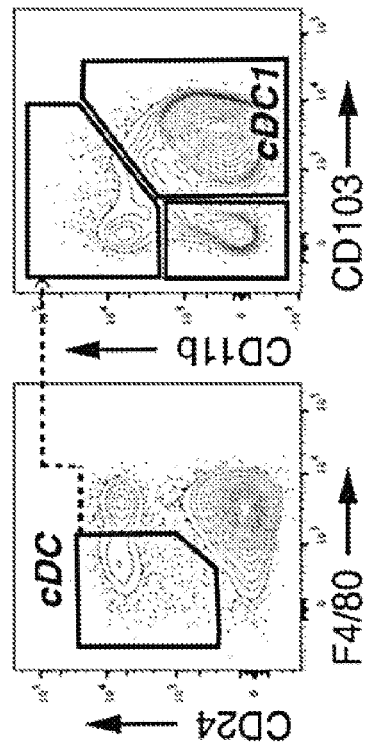
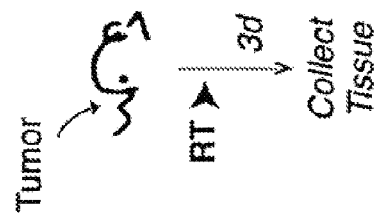
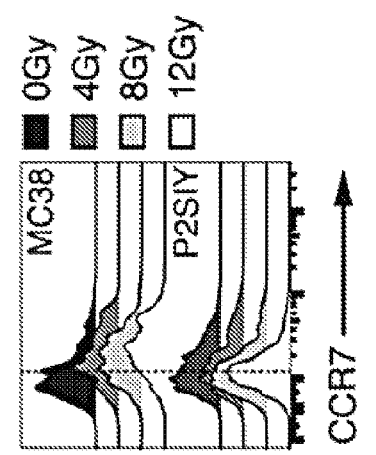
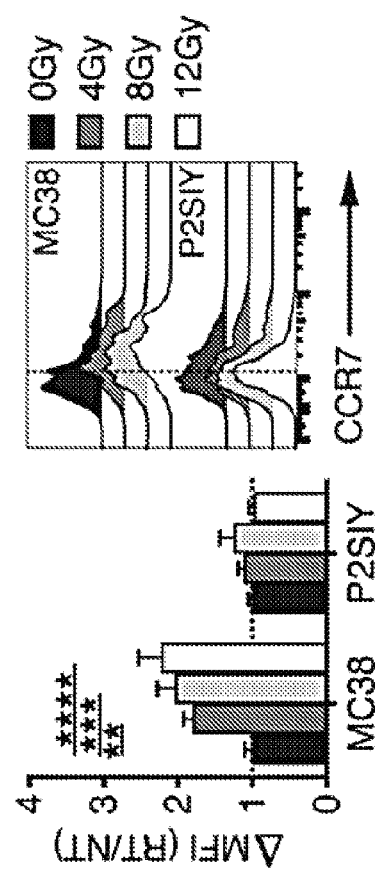

cDCs: Cluster 16 + Zbtb46

Differentially Expressed Genes

DAVID: Gene Ontology (GO) Terms

IPA: Predicted TF Activation with RT

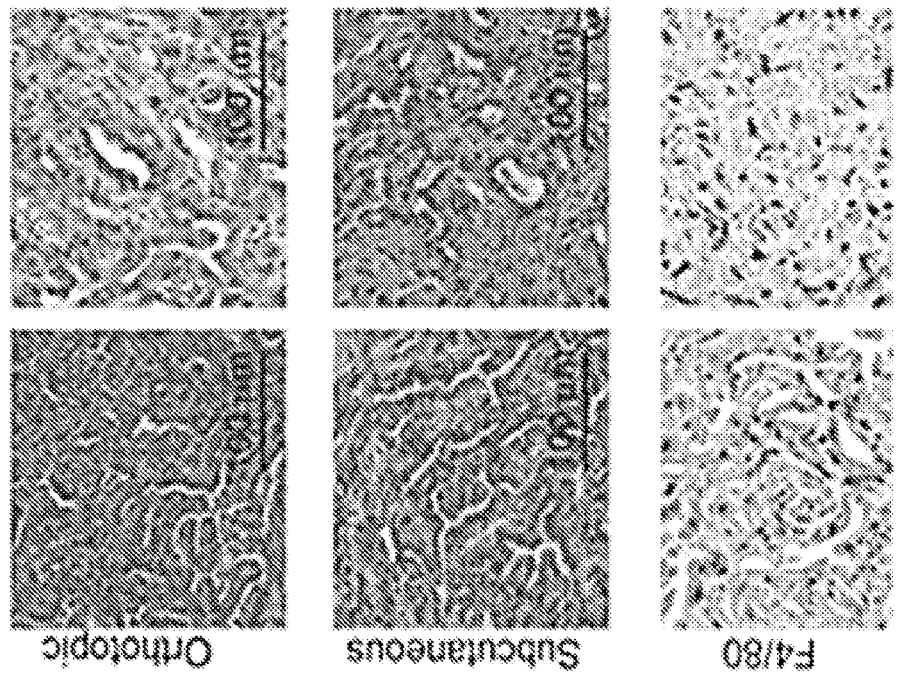
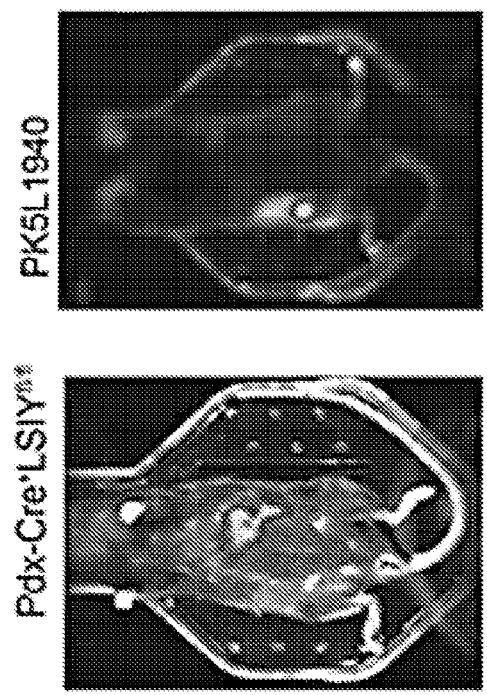

CANCER THERAPEUTIC COMPOSITIONS AND METHODS TARGETING DNASE1L3

CROSS REFERENCE TO RELATED APPLICATIONS

This application is the § 371 U.S. National Stage of International Application No. PCT/US2021/051942, filed Sep. 24, 2021, which was published in English under PCT Article 21(2), which in turn claims the benefit of U.S. Provisional Application No. 63/083,645, filed Sep. 25, 2020, which is are incorporated herein by reference in their entireties.

ACKNOWLEDGMENT OF GOVERNMENT SUPPORT

This disclosure was made with government support under Contract Nos. R01 CA182311 and R01 CA244142 awarded by the National Institutes of Health. The government has certain rights in the invention.

FIELD

The present disclosure relates to methods of treating cancer using an inhibitor of DNAse1L3, for example, in combination with radiation treatment. This disclosure also relates to methods of identifying a tumor or subject with increased likelihood of responding to an inhibitor of DNAse1L3, for example, in combination with radiation treatment.

INCORPORATION OF SEQUENCE LISTING

The Sequence Listing is submitted as an ASCII text file in the form of the file named Sequence_Listing.txt, which was created on Mar. 2, 2023, and is 4941 bytes, which is incorporated by reference herein.

BACKGROUND

Immune activation and inflammation are linked to DNA damage and repair at many levels. Nucleases that prevent cytoplasmic DNA entry and accumulation, such as DNAse2a in the endosome and TREX1 in the cytoplasm, reduce inflammation. Immune activation can also be reduced by various DNases (e.g., DNAse1L1, DNAse1L2, and DNAse1L3). DNAse1L3 has recently emerged as a tumor associated molecule and potentially promising therapeutic target.

Within the liver and spleen, DNAse1L3 is primarily expressed by dendritic cells and macrophages. Dendritic cells (DCs) play important roles in initiating and sustaining anti-cancer immunity. In addition, radiation therapy is capable of directing adaptive immune responses against tumors by stimulating the release of endogenous adjuvants and tumor-associated antigens (Blair et al., *J. Immunol.*, 2020; 204 (12): 3416-3424). Within the tumor, DCs are uniquely positioned to respond to these signals, uptake exogenous tumor antigens, and migrate to the tumor draining lymph node to initiate cross-priming of tumor-reactive cytotoxic CD8[+] T cells. Recent studies have demonstrated that administration of adjuvants that promote DC maturation and migration can improve tumor control following radiation therapy. DNAse1L3 has been shown to degrade DNA in microvesicles to limit autoimmune responses and may play an important role in limiting innate immune activation in vivo (see, e.g., Sisirak et al., *Cell.* 2016; 166 (1): 88-101; Shi et al., *Front Immunol.* 2017; 8:522; and Keyel, *Dev Biol.* 2017; 429 (1): 1-11).

SUMMARY

It is proposed herein that DNAse1L3 expressed by tumor-associated macrophages and dendritic cells functions to degrade DNA that may be released from cancer cells in the form of autophagosomes, exosomes, or additional vesicles generated following radiation therapy, including apoptotic bodies or released micronuclei. In this way, DNAse1L3 may limit the availability of nucleic acids that may act as innate immune triggers to promote functional anti-tumor immunity.

Given the potential role of DNAse1L3 in limiting anti-tumor immunity, it follows that inhibiting DNAse1L3 may serve to stimulate anti-tumor immunity, particularly when combined with treatments such as radiation therapy. In some embodiments, methods for treating a subject with cancer, including administering to the subject an effective amount of an inhibitor of DNAse1L3 and an effective amount of radiation therapy are disclosed herein. In some examples, the methods involve enhancing or inducing response of tumor-associated immune cells in the subject, including administering to the subject an effective amount of radiation therapy, and administering to the subject an effective amount of an inhibitor of DNAse1L3, thereby enhancing or inducing the response of tumor-associated immune cells in the subject. In some examples, the tumor-associated immune cells comprise dendritic cells or macrophages.

In other examples, radiation therapy is administered locally to the tumor. In some examples, the radiation therapy and the inhibitor of DNAse1L3 are administered in either order. In some examples, the inhibitor of DNAse1L3 is a direct inhibitor. In particular examples, an inhibitor of DNAse1L3 may be a direct inhibitor such as a peptide, an antibody, or a small molecule such as Fmoc-d-cyclohexyl-alanine (FCA), 4-(4,6-dichloro-[1,3,5]-triazin-2-ylamino)-2-(6-hydroxy-3-oxo-3H-xanthen-9-yl)-benzoic acid (DR396), Pontacyl Violet 6R (PV6R), or heparin. In other examples, the inhibitor of DNAse1L3 is an inhibitory RNA (RNAi) such as a DNAse1L3 antisense molecule, a DNAse1L3 shRNA molecule, a DNAse1L3 siRNA molecule, a DNAse1L3 microRNA (miRNA) molecule, or a combination thereof. In particular examples, the inhibitory RNA (RNAi) includes a nucleic acid molecule that is antisense to at least a portion of a DNAse1L3-encoding nucleic acid molecule set forth as SEQ ID NO: 1.

In some examples, the inhibitor of DNAse1L3 is administered systemically or at specific tumor locations in the subject. In other examples, a second anti-cancer therapeutic agent is also administered to the subject. In some embodiments, one or more immune-modulatory molecules (such as one or more checkpoint inhibitor or co-stimulatory molecules), for example, targeting PD-1, PD-L1 (B7-H1), CTLA-4, LAG3, or OX40, are also administered to the subject. In other examples, one or more adjuvants, antigens, vaccines, allergens, antibiotics, gene therapy vectors, vaccines, kinase inhibitors, MerTK inhibitors, TLR agonists, or TLR antagonists are also administered to the subject.

In additional embodiments, a method of identifying a tumor or a subject with a tumor for treatment with an effective amount of an inhibitor of DNAse1L3 and an effective amount of radiation therapy is provided. The disclosed methods include measuring an amount of DNAse1L3 in a sample (e.g., macrophages, dendritic cells, a tumor sample, or a blood sample) from the subject, determining an increased amount of DNAse1L3 in the sample compared to a control, and selecting the tumor or subject with the tumor for treatment. In some embodiments, the methods further include administering to the subject an effective amount of radiation therapy and administering to the subject an effective amount of an inhibitor of DNAse1L3. In some examples, measuring the amount of DNAse1L3 includes detecting DNAse1L3 nucleic acids or proteins in the sample. In some examples, the methods involve treating a subject wherein the tumor is a pancreatic adenocarcinoma or a colorectal adenocarcinoma.

The foregoing and other features of the disclosure will become more apparent from the following detailed description, which proceeds with reference to the accompanying figures.

BRIEF DESCRIPTION OF THE DRAWINGS

FIGS. 1A-1C show identification of radioimmunogenic and poorly radioimmunogenic tumors. FIG. 1A depicts overall survival rates in mice bearing aggressive MC38 colorectal adenocarcinoma tumors and Panc02-SIY pancreatic adenocarcinoma tumors. FIG. 1B depicts in vivo treatment of tumors in mice with CT-guided radiation therapy avoiding tumor-draining lymph nodes. FIG. 1C shows overall survival of mice bearing MC38 or Panc02-SIY tumors. Displayed groups include untreated (NT) subjects, subjects treated with 12Gy radiation therapy (RT), or subjects treated with radiation therapy and CD8 T cell depletion (RT+ αCD8).

FIGS. 2A-2C illustrate dendritic cell maturation in irradiated tumors. FIG. 2A depicts the experimental design, including in vivo treatment of tumors in mice with CT-guided radiation therapy. FIG. 2B depicts identification of DC1 infiltrating the tumor using flow cytometry. FIG. 2C depicts CCR7 expression on DC1 in MC38 or Panc02-SIY tumors treated with a range of radiation doses.

FIG. 2B shows differential gene expression between cDCs from different tumors/treatments, with genes increased, decreased, or not significant. FIG. 5C shows DAVID pathway analysis of genes that were significantly increased in cDCs from MC38 tumors vs P2SIY tumors following RT. FIG. 5D shows Qiagen IPA analysis of transcription factors regulating genes differentially expressed between RT cDCs from MC38 vs P2SIY cells.

FIG. 6A shows the effect of IL-4 treatment on DNAse1L3 RNA expression in bone marrow derived macrophages or dendritic cells. FIG. 6B is a schematic diagram illustrating selective Cre expression in myeloid cells, as used to generate mouse strains for conditional knockout. FIG. 6C shows DNAse1L3 activity in serum of conditional knockout mice.

FIGS. 7A-7E show tumor models generated herein. Pdx-Cre$^{+/-}$ Kras$^{(G12D)+/-}$ Trp53$^{(R172H)+/-}$ mice were crossed with Luciferase-SIY$^{fl/fl}$ mice that have pancreatic-selective bioluminescent signal and a trackable antigen (FIG. 7A). Cell lines derived from tumors in these mice were implanted as a subcutaneous tumor (FIG. 7B). FIGS. 7C-7D show pancreatic tumor histology from cell lines without (FIG. 7C) or with (FIG. 7D) Luciferase-SIY when grown as orthotopic or subcutaneous tumors, and macrophage infiltration. FIG. 7E shows RNASeq analyses of a panel of these cell lines grown in vitro (TC) or as tumors in vivo (TU) showing expression of DNAse1L3, myeloid markers, and their correlations.

SEQUENCE LISTING

Figure 3:
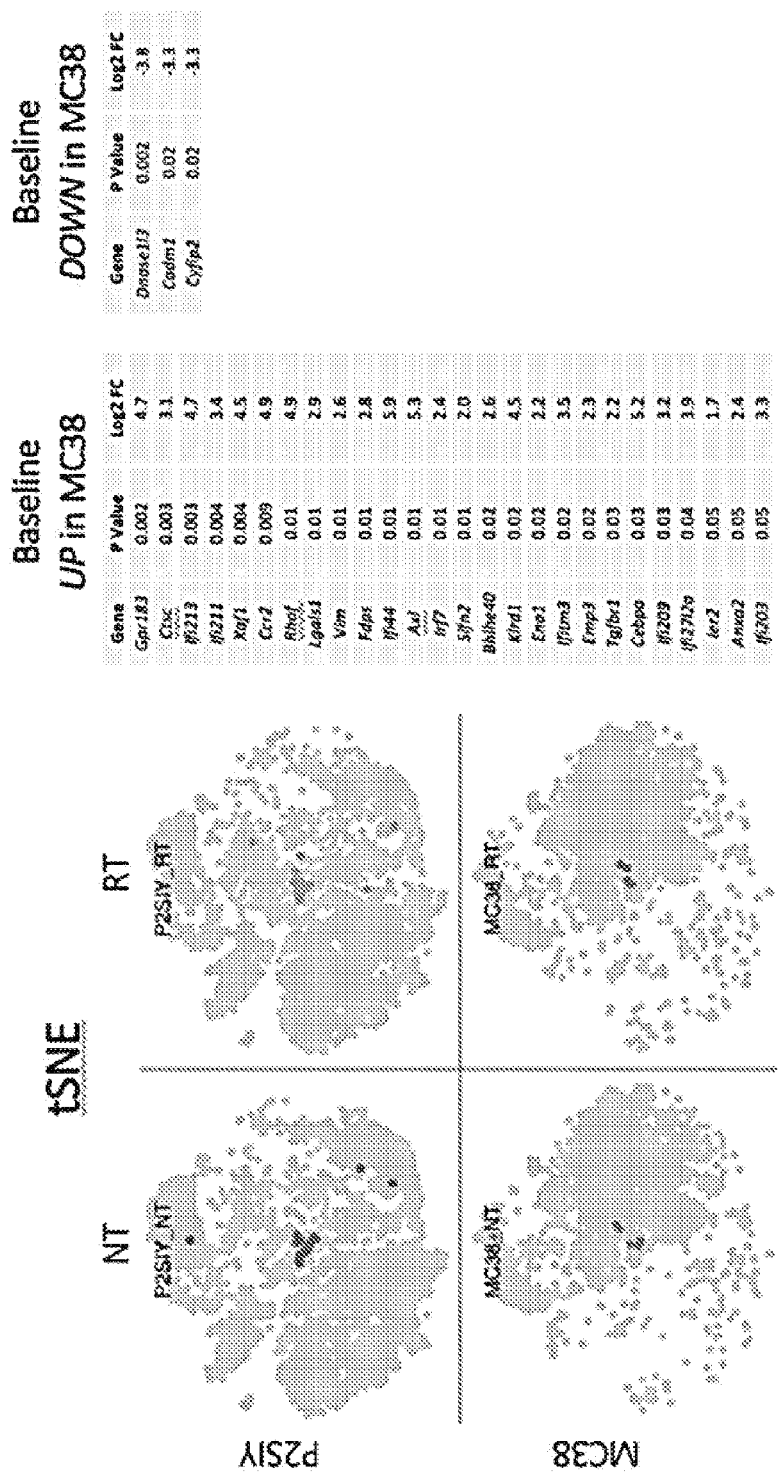
FIG. 3 depicts identification of differentially regulated genes by scRNA Seq, showing genes enriched in MC38 DC versus Panc02-SIY DC from untreated tumors (NT) or tumors treated with radiation (RT).

Any nucleic and amino acid sequences referenced herein or in the accompanying Sequence Listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is an exemplary nucleic acid sequence (Genbank Accession No. NM_004944.4) encoding human DNase1L3:

```
  1 gccagaatcc agcactccaa gcactgctgt cttctcacag agtcttgaag ccagagcagc 61 gccaggatgt cacgggagct ggccccactg ctgettetce tcctctccat ccacagegcc 121 ctggccatga ggatctgctc cttcaacgtc aggtcctttg gggaaagcaa gcaggaagac 181 aagaatgcca tggatgtcat tgtgaaggtc atcaaacgct gtgacatcat actcgtgatg 241 gaaatcaagg acagcaacaa caggatctgc cccatactga tggagaagct gaacagaaat 301 tcaaggagag gcataacgta caactatgtg attagctctc ggcttggaag aaacacatat 361 aaagaacaat atgcctttct ctacaaggaa aagctggtgt ctgtgaagag gagttatcac 421 taccatgact atcaggatgg agacgcagat gtgtttteca gggagccctt tgtggtctgg 481 ttccaatctc cccacactgc tgtcaaagac ttegtgatta tccccctgca caccacccca 541 gagacatccg ttaaggagat cgatgagttg gttgaggtct acacggacgt gaaacaccgc 601 tggaaggcgg agaatttcat tttcatgggt gacttcaatg ccggctgcag ctacgtcccc
```

```
 661 aagaaggcct ggaagaacat ccgcttgagg actgacccca ggtttgtttg gctgatcggg 721 gaccaagagg acaccacggt gaagaagagc accaacigig catatgacag galigigcut 781 agaggacaag aaatcgtcag ttctgttgtt cccaagtcaa acagtgtttt tgacttccag 841 aaagcttaca agctgactga agaggaggcc ctggatgtca gegaccactt tccagttgaa 901 tttaaactac agtcttcaag ggccttcacc aacagcaaaa aatctgtcac tctaaggaag 961 aaaacaaaga gcaaacgctc ctagacccaa gggtctcate ttattaacca tttcttgcct 1021 ctaaataaaa tgtctctaac agatatgaac tgctccctgt acttaggaaa caagagtgat 1081 ccaactgctt tcattttttg acctgaattt attctgactt gagccaaatt ggaaggagaa 1141 tcttttgtat ctctcttggt ctcataccte ccctgaattg tctaaaaggg aaccaggggc 1201 atttgtagac caaaatgatg atcttcatgc cctgagccag agcccatcc actgtcactg 1261 gccctgctca accctgtcat gcgagaggct gcaggggag gaagagcgtc agctttcagt 1321 cctcatgagg ggtcctgtte cacacgcaat gaccagaaac accaaggece cagctgcccc 1381 tgtgatttgg gcaattaact gttttaagag tctg
```

SEQ ID NO: 2 is an exemplary amino acid sequence (GenBank Accession No. NP_004935.1) of human DNase1L3:

MSRELAPLLLLLLSIHSALAMRICSFNVRSFGESKQEDKNAMDVIVKVIK

RCDIILVMEIKDSNNRICPILMEKLNRNSRRGITYNYVISSRLGRNTYKE

QYAFLYKEKLVSVKRSYHYHDYQDGDADVFSREPFVVWFQSPHTAVKD

FVIIPLHTTPETSVKEIDELVEVYTDVKHRWKAENFIFMGDFNAGCSYVP

KKAWKNIRLRTDPRFVWLIGDQEDTTVKKSTNCAYDRIVLRGQEIVSSV

VPKSNSVFDFQKAYKLTEEEALDVSDHFPVEFKLQSSRAFTNSKKSVTL

RKKTKSKRS

DETAILED DESCRIPTION

DNAse1L3 is a recently characterized DNAse that has the unique ability to degrade polynucleosomes that are encapsulated in microvesicles. Microvesicles are commonly released from cancer cells and contain a range of potential antigenic targets and immunogenic adjuvants, yet cancers grow despite active release of these microvesicles in various forms. Recent data suggests that DNAse1L3 acts to suppress the potential autoimmune consequence of microvesicles, and the results described in the instant application suggest that similar mechanisms suppress anti-tumor immunity. In particular, DNAse1L3 is upregulated in dendritic cells in tumors that fail to mature DCs and fail to generate adaptive immune responses following radiation therapy. In addition, the studies described herein show that DNAse1L3 is upregulated on M2 differentiation of macrophages. Thus, DNAse1L3 is a novel target for cancer immunotherapy, and may be particularly relevant when used in combination with radiation therapy.

Nucleic acid sensing plays an important role in regulating the immune response following radiation therapy, and cells can generate a zone of degradation in their vicinity that limits nucleic acid sensing. DNAse1L3 is secreted primarily from myeloid cells and causes degradation of DNA encapsulated in microvesicles or dying cells. Recent work has shown that the absence of DNAse1L3 through inherited mutations or acquired suppressive antibodies results in autoimmunity. These data demonstrate that microvesicles released in normal conditions are potentially immunogenic but are restrained by the action of DNAse1L3. Microvesicles are released from cancer cells at high levels and are detectible in the peripheral blood of cancer patients. These data suggest an opportunity to exploit DNAse1L3 action on DNA release and microvesicle release in cancer to direct anti-tumor immunity to the tumor. Microvesicle release from cancer cells is accentuated by cell stress and cytotoxic treatments, providing a potential tumor targeting element. Microvesicles contain bioactive DNA, and microvesicles generated following radiation therapy of cancer cells can carry tumor DNA capable of triggering STING pathways in neighboring immune dendritic cells. Thus, preventing degradation of DNA in microvesicles may improve the inflammatory environment in the irradiated tumor to sustain anti-tumor immunity.

I. Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," may refer to both the singular as well as plural, unless the context clearly indicates otherwise. As used herein, the term "comprises" can mean "includes." Thus, "comprising A or B," means "including A, B, or A and B," without excluding additional elements. Dates of GenBank® Accession Nos. referred to herein are the sequences available on Sep. 25, 2020. All references, including journal articles, patents, and patent publications, and GenBank® Accession numbers cited herein are incorporated by reference in their entirety.

Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. In order to facilitate review of the various embodiments of the disclosure, the following explanations of specific terms are provided:

Cancer: A class of diseases or conditions in which abnormal cells divide without control and can invade nearby tissues. A malignant cancer is one in which a group of tumor cells display one or more of uncontrolled growth (e.g., division beyond normal limits), invasion (e.g., intrusion on and destruction of adjacent tissues), and metastasis (e.g., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which can be measured by the number, volume, or weight of the tumor.

Dendritic Cell (DC): Refers to a type of specialized antigen presenting cell (APC) involved in innate and adaptive immunity. Dendritic cells are the principal antigen presenting cells (APCs) involved in primary immune responses. DCs include plasmacytoid dendritic cells and myeloid dendritic cells. Immature DCs originate in the bone marrow and reside in the periphery as immature cells. In the case of injury or infection, the immature DCs capture antigens, which are processed by endosomal or proteosomal pathways for presentation on the cell surface. Dendritic cells may be present in the tumor microenvironment and in some examples these are referred to as "tumor-associated dendritic cells" or "tDCs."

DNAse1L3: (e.g., OMIM 602244): Also called Deoxyribonuclease 1 Like 3, DNAS1L3, Liver and Spleen DNase, DNase I-Like 3, LSD, and DNase Gamma. DNAse1L3 has a molecular mass of 32 kDa, a basic pI of 9.5 and a pH optimum of about 7. It is an endonuclease and cleaves double-stranded DNA (and single-stranded DNA) producing 3'-OH/5'-P ends, and is $Ca^{2+}/Mg^{2+}$-dependent. DNAse1L3 is present in the blood, though it is primarily secreted by myeloid cells. Within the liver and spleen, DNAse1L3 is primarily expressed by dendritic cells and macrophages. In humans, DNAse1L3 is encoded by the DNASE1L3 gene on chromosome 3. Expression of the DNASE1L3 gene has been verified for the spleen, liver, thymus, lymph node, bone marrow, small intestine and kidney. At the cellular level, DNASE1L3 gene expression has been verified for spleen macrophages, kidney, thymus and intestine, as well as for hepatic Kupffer cells.

DNAse1L3 sequences are publicly available, for example from the GenBank® sequence database, e.g., Accession Nos. NP_001243489.1, NP_004935.1 (SEQ ID NO:2), NP_001366.1, and AAH15831.1 provide exemplary human DNAse1L3 protein sequences, while Accession Nos. NM_001256560.2 and NM_004944.4 (SEQ ID NO: 1) provide exemplary human DNAse1L3 nucleic acid sequences). One of ordinary skill in the art can identify additional DNAse1L3 nucleic acid and protein sequences, including DNAse1L3 variants, such as those having at least 80%, at least 85%, at least 90%, at least 92%, at least 95%, at least 98%, or at least 99% sequence identity to these GenBank® sequences, such as at least 80%, at least 85%, at least 90%, at least 92%, at least 95%, at least 96%, at least 97%, at least 98%, or at least 99% sequence identity to SEQ ID NO: 1 or 2.

Effective amount/therapeutically effective amount): The amount of an agent (e.g., DNAse1L3 inhibitors disclosed herein, radiation therapy, or other anti-cancer agents) that is sufficient to effect at least one beneficial or desired therapeutic result, including clinical results.

An effective amount may vary depending upon one or more of: the subject and disease condition being treated, the sex, weight and age of the subject, the severity of the disease condition, the manner of administration, the ability of the treatment to elicit a desired response in the individual, and the like. The beneficial therapeutic effect can include contributing to diagnostic determinations; amelioration of a disease, symptom, disorder, or pathological condition; reducing or preventing the onset of a disease, symptom, disorder or condition; and/or generally counteracting a disease, symptom, disorder or pathological condition.

The term "effective amount" includes an amount that is effective to "treat" a subject (e.g., a patient). When a therapeutic amount is indicated, the precise amount of the compositions of the present disclosure to be administered can be determined by a physician with consideration of individual differences in age, weight, tumor size, extent of infection or metastasis, and condition of the patient (subject).

In one embodiment, an "effective amount" (e.g., of an inhibitor of DNAse1L3, or radiation therapy described herein) may be an amount sufficient to reduce the volume/size of a tumor, the weight of a tumor, the number/extent of metastases, reduce the volume/size of a metastasis, the weight of a metastasis, or combinations thereof, for example by at least about 10%, at least about 20%, at least about 25%, at least about 50%, at least about 70%, at least about 75%, at least about 80%, at least about 90%, at least about 95%, or at least about 99% (as compared to no administration of the therapeutic agent). In one embodiment, an "effective amount" (e.g., of an inhibitor of DNAse1L3, or radiation therapy described herein) may be an amount sufficient to increase the survival time of a subject, such as a subject with cancer, for example by at least about 10%, at least about 20%, at least about 25%, at least about 50%, at least about 70%, at least about 75%, at least about 80%, at least about 90%, at least about 95%, 100%, 200%, 300%, 400%, or 500% (as compared to no administration of the therapeutic agent).

Immune cell: Any cell of the immune system that has one or more effector functions (e.g., cytotoxic cell killing activity, secretion of cytokines, induction of ADCC and/or CDC).

Macrophages: Macrophages are a type of white blood cell of the immune system that engulfs and digests cellular debris, foreign substances, microbes, cancer cells, and the like. These phagocytes include various subtypes (e.g., histiocytes, Kupffer cells, alveolar macrophages, microglia, and others), but all are part of the mononuclear phagocyte system. Besides phagocytosis, they play a critical role in both innate and adaptive immunity by recruiting other immune cells such as lymphocytes. For example, they are important as antigen presenters to T cells. Macrophages that encourage inflammation are called M1 macrophages, whereas those that decrease inflammation and encourage tissue repair are called M2 macrophages.

Radiation therapy: A treatment for cancer utilizing localized high doses of radiation to kill cancer cells and/or shrink tumors. Radiation has been demonstrated to induce adaptive immune responses to mediate tumor regression. In particular examples, radiation therapy includes external beam therapy (for example, delivery of a beam of high-energy x-rays to the location of a tumor). Examples of external beam therapy include intensity-modulated radiation therapy (IMRT), which uses proton beams of varying intensities to precisely irradiate a tumor. IMRT provides fine control of radiation intensity and beam shape such that exposure of healthy tissue to radiation is limited.

Subject/Individual/Patient: A vertebrate, such as a mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, guinea pig, pig, goat, sheep, dog, cat, horse, or cow. In some examples, the subject has a tumor, such as a cancer, that can be treated using the DNAse1L3 inhibitors disclosed herein. In some examples, the subject is a laboratory animal/organism, such as a mouse, rabbit, guinea pig, or rat. In one example a subject includes farm animals and domestic animals or companion animals (such as a cat or dog). In one example, a subject is a human patient that has a cancer, has been diagnosed with a cancer, or is at risk of having a cancer. A "patient" can refer to a subject that has been diagnosed with a particular indication that can be treated with DNAse1L3 inhibitors and methods disclosed herein.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of progression or decline, making the final point of progression less debilitating, improving a subject's physical or mental well-being, or prolonging the length of survival. Treatment does not necessarily indicate complete eradication or cure of the disease or condition, or associated symptoms thereof. The treatment may be assessed by objective or subjective parameters; including the results of a physical examination, blood and other clinical tests (such as imaging), and the like. In some examples, treatment with the disclosed methods results in a decrease in the number, volume, and/or weight of a tumor and/or metastases.

Vector: A nucleic acid molecule that can be introduced into a host cell (for example, by transfection or transduction), thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function.

II. DNAse1L3 Inhibitors

The methods disclosed herein utilize one or more inhibitors of DNAse1L3, for example for treatment of cancer. As used herein, the terms "DNAse1L3 inhibitor" or "inhibitor of DNAse1L3" refer to a small organic molecule, nucleic acid, peptide, compound, antibody, or antibody fragment that binds to and/or inhibits at least one activity of DNAse1L3, such as single-stranded nucleolytic cleavage of DNA. In one embodiment, inhibition of DNAse1L3 is achieved by occupancy-based inhibition of DNAse1L3 protein or target RNA degradation. In one embodiment, a DNAse1L3 inhibitor interferes with divalent ion-dependent function in DNAse1L3. In some examples, a DNAse1L3 inhibitor is specific for one or more isoforms of DNAse1L3, while in other examples, a DNAse1L3 inhibitor does not display isoform selectivity and is considered a "pan-DNAse1L3 inhibitor." An inhibitor that only targets DNAse1L3 can be referred to as a selective DNAse1L3 inhibitor. One example of a selective DNAse1L3 inhibitor is DR396 (see, e.g., Zykova et al., *PLoS ONE*. 2010; 5 (8): e12096). Exemplary DNAse1L3 inhibitors are provided herein; however, one of ordinary skill in the art can identify other DNAse1L3 inhibitors that can be used in the methods described herein.

In one example, inhibition of DNAse1L3 increases tumor-associated dendritic cell maturation, for example, as compared to DC maturation in the absence of the inhibitor. In another example, inhibition of DNAse1L3 increases the DNA component of NETs (e.g., nuclear DNA associated with histones). In another example, inhibition of DNAse1L3 decreases chromatin fragmentation in cells undergoing apoptosis. In another example, inhibition of DNAse1L3 blocks both NLR family, pyrin domain containing 3 (NLRP3) and NLRC4 inflammasome-mediated release of high-mobility group box 1 protein and IL-1β. In another example, DNAse1L3 inhibition impairs NLRP3-dependent pyroptosis (see, e.g., Lazzaretto et al., *J. Immunol.* 2019; 203:2276-2290; Sisirak et al., *Cell.* 2016; 166 (1): 88-101; Shi et al., *Front Immunol.* 2017; 8:522).

The DNAse1L3 inhibitor may be a direct inhibitor of DNAse1L3. A direct DNAse1L3 inhibitor is an agent that binds directly to DNAse1L3 protein or nucleic acid, thereby inhibiting, decreasing, or reducing one or more activities of DNAse1L3. In one embodiment, a direct DNAse1L3 inhibitor can be understood to refer to an agent that exhibits a 50% inhibitory concentration with respect to DNAse1L3 that is at least 10-fold, at least 20-fold, at least 30-fold, at least 50-fold, at least 100-fold, at least 1000-fold, or more, lower than the inhibitor's IC50 with respect to other proteins in the DNAse1L3 pathway.

In particular embodiments, a direct inhibitor of DNAse1L3 includes a small molecule, an antibody or antibody fragment, a DNAse1L3 aptamer, or a combination of two or more thereof. In one example, a direct inhibitor of DNAse1L3 is a small molecule that binds to at least a portion of DNAse1L3. Small molecules refer to a composition that has a molecular weight of less than about 5 kD (such as less than about 5 kD, less than about 2.5 kD, less than about 1 kD, or less than about 500 Daltons) and may include peptidomimetics, peptoids, carbohydrates, lipids, components thereof or other organic or inorganic molecules. Non-limiting examples of small molecule inhibitors of DNAse1L3 are Fmoc-d-cyclohexylalanine (FCA), 4-(4,6-dichloro-[1,3,5]-triazin-2-ylamino)-2-(6-hydroxy-3-oxo-3H-xanthen-9-yl)-benzoic acid (DR396), Pontacyl Violet 6R (PV6R), and heparin.

In particular examples, a direct inhibitor of DNAse1L3 is an antibody that binds to an epitope of DNAse1L3 (such as an epitope of human DNAse1L3). The term "antibody" is used herein in the broadest sense and encompasses various antibody structures, including but not limited to monoclonal antibodies, polyclonal antibodies, multi-specific antibodies (e.g., bispecific antibodies), and antigen binding fragments, so long as they exhibit the desired antigen binding activity. Non-limiting examples of antibodies include, for example, intact immunoglobulins and variants and fragments thereof that retain binding affinity for the antigen. Examples of antigen binding fragments include but are not limited to Fv, Fab, Fab', Fab'-SH, F(ab')$_2$, diabodies, linear antibodies, single-chain antibody molecules (e.g. scFv), and multispecific antibodies formed from antibody fragments. Antibody fragments include antigen binding fragments either produced by the modification of whole antibodies or those synthesized de novo using recombinant DNA methodologies (see, e.g., Kontermann and Dübel (Eds.), *Antibody Engineering*, Vols. 1-2, $2^{nd}$ ed., Springer-Verlag, 2010). Antibodies also include genetically engineered forms, such as chimeric antibodies (such as humanized murine antibodies) and heteroconjugate antibodies (such as bispecific antibodies).

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies. In some examples monoclonal antibodies are isolated from a subject. Monoclonal antibodies can have conservative amino acid substitutions which have substantially no effect on antigen binding or other immunoglobulin functions. See, for example, Greenfield (Ed.), *Antibodies: A Laboratory Manual*, $2^{nd}$ ed. New York: Cold Spring Harbor Laboratory Press, 2014.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* $1^{st}$ Ed. New York: Cold Spring Harbor Laboratory Press, 2004; Lonberg, *Nat. Biotech.*, 23:1117-1125, 2005; Lonberg, *Curr. Opin. Immunol.*, 20:450-459, 2008).

Antibodies that bind to DNAse1L3 are commercially available, and include antibodies for DNASE1L3 available from Biorbyt (e.g., catalog numbers orb100610, orb29519, orb31970, orb258915), Creative Diagnostics (e.g., catalog numbers DCAGH-4308 and DCABH-11306), GeneTex (e.g., catalog number GTX114363), Thermo Fisher Scientific (e.g., catalog numbers PA5-107133, PA5-30006, 11330-1-AP, and BS-7653R)), and OriGene (e.g., catalog number TA349899). Methods of producing antibodies to a protein of interest are also known to one of ordinary skill in the art.

In one example, a direct inhibitor of DNAse1L3 is an inhibitory RNA (RNAi), such as a DNAse1L3 antisense molecule, a DNAse1L3 shRNA molecule, a DNAse1L3 siRNA molecule, a DNAse1L3 microRNA (miRNA) molecule, or combinations thereof. RNAi is a form of antisense mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs. In some embodiments, non-limiting examples of inhibitory RNA (RNAi) of DNAse1L3 includes a nucleic acid molecule that is antisense to at least a portion of a DNAse1L3-encoding nucleic acid molecule (such as SEQ ID NO: 1), a DNAse1L3 shRNA, a DNAse1L3 siRNA (e.g., polyethylenimine (PEI)-based nanoparticle encapsulated siRNA; ON-TARGETplus DNASE1L3 siRNA pool (L-012694-00; Dharmacon)), and a miRNA that targets DNAse1L3.

III. Methods of Treatment

Disclosed herein are methods of treating cancer utilizing a combination of an inhibitor of DNAse1L3 and radiation therapy. In some embodiments, the methods include administering to the subject an effective amount of a DNAse1L3 inhibitor (e.g., a composition including a DNAse1L3 inhibitor and a pharmaceutically acceptable carrier) and an effective amount of radiation therapy, such as at least one dose of radiation therapy. In some embodiments, the disclosed methods enhance or increase a response of tumor-associated immune cells in the subject. In some examples, the methods include administering to the subject an effective amount of a DNAse1L3 inhibitor before or after radiation therapy. In some embodiments, an effective amount of an inhibitor of DNAse1L3 is administered 0-5 days following radiation therapy. In some embodiments, an effective amount of inhibitor of DNAse1L3 is administered in phases or cycles according to the pharmacology or toxicity profile.

In particular embodiments, said tumor-associated immune cells include dendritic cells or macrophages. Further, "enhancing or increasing a response" refers generally to the ability of a composition to produce, elicit, or cause a greater physiological response (e.g., downstream effects) compared to the response caused by either vehicle or a control molecule/composition. A measurable physiological response may include inducing response of tumor-associated immune cells in the subject and/or an increase in cancer cell death killing ability, among others apparent from the understanding in the art and the description herein. An "enhanced" or "increased" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by a vehicle or a control composition.

In particular examples, the subject has a hematological malignancy. Exemplary hematological malignancies include leukemias, including acute leukemias (such as 11q23-positive acute leukemia, acute lymphocytic leukemia (ALL), T-cell ALL, acute myelocytic leukemia, acute myelogenous leukemia (AML), and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), lymphoblastic leukemia, polycythemia vera, lymphoma, diffuse large B cell lymphoma, Burkitt lymphoma, T cell lymphoma, follicular lymphoma, mantle cell lymphoma, Hodgkin disease, non-Hodgkin lymphoma, multiple myeloma, Waldenstrom macroglobulinemia, heavy chain disease, myelodysplastic syndrome, hairy cell leukemia, and myelodysplasia. In particular examples, the subject may have a myeloid leukemia (such as AML) or a B cell malignancy.

In other examples, the subject has a solid tumor. Examples of solid tumors include sarcomas (such as fibrosarcoma, myxosarcoma, liposarcoma, chondrosarcoma, osteogenic sarcoma, and other sarcomas), synovioma, mesothelioma, Ewing sarcoma, leiomyosarcoma, rhabdomyosarcoma, colon cancer, colorectal cancer, peritoneal cancer, esophageal cancer, pancreatic cancer, breast cancer (including basal breast carcinoma, ductal carcinoma and lobular breast carcinoma), lung cancer, ovarian cancer, prostate cancer, liver cancer (including hepatocellular carcinoma), gastric cancer, squamous cell carcinoma (including head and neck squamous cell carcinoma), basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, hepatoma, bile duct carcinoma, choriocarcinoma, Wilms tumor, cervical cancer, fallopian tube cancer, testicular tumor, seminoma, bladder cancer (such as renal cell cancer), melanoma, and CNS tumors (such as a glioma, glioblastoma, astrocytoma, medulloblastoma, craniopharyrgioma, ependymoma, pinealoma, hemangioblastoma, acoustic neuroma, oligodendroglioma, meningioma, neuroblastoma and retinoblastoma). Solid tumors also include tumor metastases (for example, metastases to the lung, liver, brain, or bone). In some examples, the subject has a cancer where there is an indication for radiation therapy. In some examples, the tumor is an adenocarcinoma. In particular non-limiting examples, the tumor is a pancreatic cancer (e.g., a pancreatic adenocarcinoma), breast cancer or a colorectal cancer.

A variety of pharmaceutically acceptable carriers can be used in the compositions provided herein, for example, buffered saline and the like, for introducing the inhibitor of DNAse1L3 to a subject. These solutions are sterile and generally free of undesirable matter. The compositions may be sterilized. In some examples, the compositions also include pharmaceutically acceptable auxiliary substances such as pH adjusting and buffering agents, toxicity adjusting agents, and preservatives, for example, sodium acetate, sodium chloride, potassium chloride, calcium chloride, sodium lactate and the like. The concentration in these formulations can vary, and will be selected primarily based on fluid volumes, viscosities, body weight and the like, in accordance with the particular mode of administration selected and the subject's needs.

The DNAse1L3 inhibitor may be administered to a subject by any suitable route, including parenteral or other routes (such as dermal adsorption or inhalation). Exemplary routes of administration include, but are not limited to, oral, injection (such as subcutaneous, intramuscular, intradermal, intraperitoneal, and intravenous) and topical routes. In some examples, the inhibitor of DNAse1L3 is administered locally, for example by direct injection to a tumor or close to a tumor.

In particular examples, the radiation therapy includes external beam therapy (for example, delivery of a beam of high-energy x-rays to the location of a pancreatic and colorectal adenocarcinoma tumor). In other examples, the radiation therapy includes intensity-modulated radiation therapy (IMRT), which is able to focus more precisely so that fewer healthy cells are destroyed than is the case with 2D or 3D conformal radiation. IMRT reduces incidental damage to the structures near the tumor that may not be involved. Methods and therapeutic dosages of radiation therapy are known to those skilled in the art and can be determined by a skilled clinician. The type of radiation therapy and the precise amount of radiation to be administered can be determined by a physician with consideration of factors such as individual differences in age, weight, type of tumor, tumor size, metastasis (if present), and condition of the subject.

In additional embodiments, the disclosed methods further include administering one or more additional treatments to the subject. The additional treatment may include one or more chemotherapeutic agents and/or immunotherapies. In another embodiment, one or more adjuvants, antigens, vaccines, allergens, antibiotics, gene therapy vectors, vaccines, kinase inhibitors, and co-stimulatory molecules is also administered to the subject. In some embodiments, a second anti-cancer therapeutic agent is also administered to the subject. The second anti-cancer therapeutic agent in some examples includes chemotherapy agents, such as anti-neoplastic chemotherapeutic agents, antibiotics, alkylating agents and antioxidants, kinase inhibitors, and other agents. Particular examples of additional therapeutic agents that can be used include microtubule binding agents (such as paclitaxel, docetaxel, vinblastine, vindesine, vinorelbine (navelbine), the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof), DNA and/or RNA transcription inhibitors (such as actinomycin D, daunorubicin, doxorubicin and derivatives and analogs thereof), antibodies (such as trastuzumab, bevacizumab, cetuximab, panitumumab), enzymes, enzyme inhibitors (such as camptothecin, etoposide, formestane, trichostatin and derivatives and analogs thereof), kinase inhibitors (such as imatinib, gefitinib, and erolitinib), and gene regulators (such as raloxifene, 5-azacytidine, 5-aza-2'-deoxycytidine, tamoxifen, 4-hydroxytamoxifen, mifepristone and derivatives and analogs thereof). Methods and therapeutic dosages of such agents are known to those skilled in the art and can be determined by a skilled clinician.

In some embodiments, the second anti-cancer therapeutic agent is an immune modulatory molecule. In particular examples, immune modulatory molecules target one or more of PD-1, PD-L1 (B7-H1), OX40/OX-40L, CTLA-4, and LAG3. Other targets may include, but are not limited to PD-2, PD-L2, IDO 1 and 2, CTNNB1 (β-catenin), SIRPα, VISTA, RNASE H2, DNase II, CLEVER-1/Stabilin-1, LIGHT, HVEM, TIM3, TIGIT, Galectin-9, KIR, GITR, TIM1, TIM4, CEACAM1, CD27, CD40/CD40L, CD48, CD70, CD80, CD86, CD112, CD137 (4-1BB), CD155, CD160, CD200, CD226, CD244 (2B4), CD272 (BTLA), B7-H2, B7-H3, B7-H4, B7-H6, ICOS, A2aR, A2bR, HHLA2, ILT-2, ILT-4, gp49B, PIR-B, HLA-G, and ILT-2/4. Other targets include MDR1, Arginase1, iNOs, IL-10, TGF-β, pGE2, STAT3, VEGF, KSP, HER2, Ras, EZH2, NIPP1, PP1, TAK1 and PLK1. Particular checkpoint inhibitors are also contemplated, including BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31 (suppl): 3000), durvalumab (AstraZeneca; also known as EVIFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., Cell Discov. 7:3 (March 2017), LY3300054 (Eli Lilly Co.; see, e.g., WO 2017/034916), and CK-301 (Checkpoint Therapeutics; see Gorelik et al., AACR: Abstract 4606 (April 2016)), pembrolizumab (also known as KEYTRUDA®, lambrolizumab, and MK-3475), nivolumab (formerly designated 5C4, BMS-936558, MDX-1106, or ONO-4538), cemiplimab (anti-PD1), and ipilimumab (anti-CTLA-4).

In some embodiments, one or more chemotherapies, adjuvants, antigens, vaccines, allergens, antibiotics, gene therapy vectors, vaccines, kinase inhibitors, checkpoint inhibitors, co-stimulatory molecules, TLR agonists, or TLR antagonists is also administered to the subject. In particular examples, inhibitors of Mertk are also administered to the subject. MER proto-oncogene tyrosine kinase (MerTK) is a macrophage-specific phagocytic cell surface receptor of the TAM-RTK family (Tyro3/AXL/MerTK Receptor Tyrosine Kinases). Inhibition of MerTK is known to suppress phagocytosis of apoptotic bodies after radiotherapy, thereby stimulating secondary necrosis and induction of inflammatory and immunogenic cell death. Autoimmune propensity is also increased in both Mertk−/− animals and DNAse1L3−/− animals.

Inhibition of MerTK with MerTK antibodies can promote antitumor effects when combined with radiation. MER proto-oncogene tyrosine kinase (MerTK) is a macrophage-specific phagocytic cell surface receptor of the TAM-RTK family (Tyro3/AXL/MerTK Receptor Tyrosine Kinases). Inhibition of MerTK is known to suppress phagocytosis of apoptotic bodies after radiotherapy, thereby stimulating secondary necrosis and induction of inflammatory and immunogenic cell death. In particular examples, MerTK inhibitors include small molecules (e.g., Warfarin; inhibits MerTK signaling), MerTK-specific antibodies (e.g., DCABY-3966 and TA5663-100u), antibody fragments, MerTK aptamers, or a combination of two or more thereof. In some embodiments, MerTK inhibitors can be administered with MerTK/Axl inhibitors (e.g., S49076) and MerTK-specific antibodies to provide enhanced immune-mediated responses to radiotherapy. MerTK-specific antibodies are commercially available, including antibodies for MerTK available from LSBio (e.g., catalog number LS-B4445), G Biosciences (e.g., ITA5663-100u and ITA7405-100u), and Creative Diagnostics (e.g., catalog number DCABY-3966).

IV. Methods of Selecting a Subject

In some embodiments, the methods include measuring an amount of DNAse1L3 in macrophages, dendritic cells, a tumor sample, or blood from the subject, determining an increased amount of DNAse1L3 in the dendritic cells or the tumor sample compared to a control, and selecting the subject as likely to respond to the methods of treatment disclosed herein. In particular embodiments, the methods further include treating the selected subject by administering to the subject an effective amount of radiation therapy and administering to the subject an effective amount of an inhibitor of DNAse1L3.

In a particular embodiment, measuring the amount of DNAse1L3 comprises detecting DNAse1L3 nucleic acid (e.g., DNA or RNA) or proteins in the dendritic cells or tumor sample. Methods of directly determining the amount of a protein (such as DNAse1L3) or RNA (such as DNAse1L3 mRNA) in a sample are known to those of skill in the art.

i. Detecting DNAse1L3 Protein

Methods of directly measuring the amount of a given protein (such as DNAse1L3) are also known in the art. The inventors have identified DNAse1L3 protein as expressed in macrophages and dendritic cells in tumors of pancreatic and colorectal adenocarcinoma. In some embodiments, the disclosed methods utilize detection of DNAse1L3 protein in a sample (such as a tumor sample or immune cells such as dendritic cells) or secreted into the serum and detected in a blood sample.

In some embodiments, DNAse1L3 is detected in the sample by immunoassay, such as ELISA, Western blot, RIA assay, or flow cytometry. The amount of DNAse1L3 can be assessed in the sample and optionally in adjacent non-tumor tissue or in tissue from cancer-free subjects. The DNAse1L3 protein in the sample can be compared to levels of the protein found in cells from a cancer-free subject or other control (such as a standard value or reference value). A significant increase or decrease in the amount can be evaluated using statistical methods known in the art. Quantitative spectroscopic methods, such as SELDI, can also be used to analyze DNAse1L3 protein expression in a sample. In one example, surface-enhanced laser desorption-ionization time-of-flight (SELDI-TOF) mass spectrometry is used to detect protein expression, for example by using the ProteinChip™ (Ciphergen Biosystems, Palo Alto, CA). Such methods are well known in the art (for example see U.S. Pat. Nos. 5,719,060; 6,897,072; and 6,881,586). SELDI is a solid phase method for desorption in which the analyte is presented to the energy stream on a surface that enhances analyte capture or desorption.

In one example, the methods include determining whether a sample from the subject has an increased amount (such as an increase of at least about 1.5-fold, 2-fold, 3-fold, 4-fold, 5-fold, 10-fold, or more) of DNAse1L3 protein relative to a control (such as a non-tumor sample of the same tissue type or a reference value or range of values for DNAse1L3 protein amount in an appropriate normal tissue). Thus, for example, if the sample from the subject is a pancreas tumor tissue sample, the control can be normal pancreas tissue, for example from the same subject or a subject without cancer, or a reference value representing a DNAse1L3 protein amount expected in a normal pancreas tissue sample. In some embodiments, the control is a pancreas tissue sample obtained from a healthy subject or a non-metastatic pancreas tissue sample obtained from a patient diagnosed with cancer.

In other embodiments, the control is a historical control or standard reference value or range of values (such as a previously tested control sample, such as a group of samples that represent baseline or normal values, such as the DNAse1L3 protein amount in non-tumor tissue). In particular examples, the methods disclosed herein provide for highly sensitive detection of DNAse1L3 protein in a biological sample.

ii. Detecting DNAse1L3 Nucleic Acids

Methods for determining the amount of DNAse1L3 DNA or RNA are known to those of skill in the art. In some examples, the methods include in situ hybridization (such as fluorescent, chromogenic, or silver in situ hybridization), or polymerase chain reaction (such as real-time quantitative PCR). In particular embodiments, ISH is used to determine the amount of DNAse1L3 nucleic acid in a sample. In another embodiment, nucleic acid amplification is used to determine the amount of DNAse1L3 nucleic acid in a sample. These methods below permit both the detection of DNAse1L3 DNA or RNA, though DNA will be primarily used for reference.

In one embodiment, DNAse1L3 DNA may be detected by in situ hybridization (ISH), such as fluorescence in situ hybridization (FISH), chromogenic in situ hybridization (CISH), or silver in situ hybridization (SISH). For example, using FISH, a DNA probe (such as an DNAse1L3 probe) is labeled with a fluorescent dye or a hapten (usually in the form of fluor-dUTP or hapten-dUTP that is incorporated into the DNA using enzymatic reactions, such as nick translation or PCR). The labeled probe is hybridized to chromosomes or nuclei on slides under appropriate conditions. After hybridization, the labeled chromosomes or nuclei are visualized either directly (in the case of a fluor-labeled probe) or indirectly (using fluorescently labeled anti-hapten antibodies to detect a hapten-labeled probe). In the case of CISH, the probe is labeled with a hapten (such as digoxigenin, biotin, or fluorescein) and hybridized to chromosome or nuclear preparations under appropriate conditions. The probe is detected with an anti-hapten antibody, which is either conjugated to an enzyme (such as horseradish peroxidase or alkaline phosphatase) that produces a colored product at the site of the hybridized probe in the presence of an appropriate substrate, or with a secondary antibody conjugated to the enzyme. SISH is similar to CISH, except that the enzyme (such as horseradish peroxidase) conjugated to the antibody (either anti-hapten antibody or a secondary antibody) catalyzes deposition of metal nanoparticles (such as silver or gold) at the site of the hybridized probe.

In other examples, the DNAse1L3 DNA is detected in a sample from the subject, for example by ISH. DNAse1L3-specific probes are well known in the art and include commercially available probes, such DNASE1L3 (20554_s_at_1) (Affymetrix), DNASE1L3 (20554_s_at_2) (Affymetrix), DNASE1L3 (20554_s_at_3) (Affymetrix), DNASE1L3 (20554_s_at_4) (Affymetrix), and DNASE1L3 (20554_s_at_5) (Affymetrix). In one embodiment, the DNAse1L3 gene may be detected on a single slide or tissue section. In one embodiment, DNAse1L3 and a second gene of interest (e.g., a gene in the DNAse1L3 signaling pathway, or IL-4 RNA) are detected with two different detectable labels for dual color assay (such as two different fluorophores, two different chromogens, or a chromogen and metal nanoparticles). The DNAse1L3 DNA and a second gene may be detected with the same label for single color assay. DNAse1L3 DNA copy number may also be determined by counting the number of fluorescent, colored, or silver spots on the chromosome or nucleus.

In another example, the amount of DNAse1L3 DNA may be determined by real-time quantitative PCR (RT-qPCR). See, e.g., U.S. Pat. No. 6,180,349. In general, the method measures PCR product accumulation through a dual-labeled fluorogenic probe (e.g., TAQMAN® probe). Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan® PCR typically utilizes the 5'-nuclease activity of Taq or Tth polymerase to hydrolyze a hybridization probe bound to its target site, but any enzyme with equivalent 5' nuclease activity can be used. Two oligonucleotide primers are used to generate a transcript typical of a PCR reaction. A third oligonucleotide, or probe, is designed to detect nucleotide sequences located between the two PCR primers. The probe is non-extendible by Taq DNA polymerase enzyme and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments dissociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data. The DNA copy number is determined relative to a normalization gene contained within the sample, which has a known copy number (see Heid et al., Genome Research 6:986-994, 1996). Quantitative PCR is also described in U.S. Pat. No. 5,538,848. Related probes and quantitative amplification procedures are described in U.S. Pat. Nos. 5,716,784 and 5,723,591.

iii. Administration of Treatment for a Subject

In additional embodiments, the method further includes selecting a treatment for the subject based on the amount of DNAse1L3 nucleic acid or protein determined by the disclosed methods. The disclosed methods may further include administering the selected treatment to the subject. It is known in the art that treatment may be selected for a subject based on the amount of a particular gene or protein present or the copy number of particular genes in a sample from the subject. For example, if the gene or protein for which the amount of nucleic acid or protein is scored is DNAse1L3, and the sample has increased (or amplified) levels of DNAse1L3 protein and/or DNAse1L3 nucleic acid, the selected therapy may include one or more inhibitors of DNAse1L3, in combination with radiation therapy, as disclosed herein.

EXAMPLES

The following examples are provided to illustrate certain particular features and/or embodiments. These examples should not be construed to limit the disclosure to the particular features or embodiments described.

Example 1

Identification of Radioimmunogenic and Poorly Radioimmunogenic Tumors

Different tumor types respond very differently to radiation therapy in vivo, and this is not due to differences in the intrinsic radiosensitivity of the cancer cells, since MC38 (colorectal cancer) and Panc02-SIY (pancreatic adenocarcinoma) cells are equally sensitive to radiation therapy in vitro (FIG. 1A). To test their response to radiation therapy in vivo, tumors were established in cohorts of genetically identical mice, and radiation therapy was targeted to the tumor, taking care to avoid the tumor-draining lymph node (FIG. 1B). Notably, a proportion of mice bearing the MC38 colorectal cancer model were cured by radiation therapy, while there was no cure in mice bearing the Panc02-SIY pancreatic adenocarcinoma model (FIG. 1C). The mechanism of action in MC38 was via CD8 T cells, since CD8 T cell depletion removed the effect. In addition, there was no consequence of CD8 T cell depletion in Panc02-SIY (FIG. 1C), suggesting that T cells are not participating in tumor control in this model.

Example 2

Identification of Radioimmunogenic Panc02-SIY Tumor Cells

Following radiation therapy in the Panc02-SIY tumor model, the DC1 population of dendritic cells (FIG. 2A) failed to mature as determined by upregulation of CCR7. This resulted in defective migration to tumor-draining lymph nodes, and defective T cell control of residual cancer cells. In mice treated with CT-guided radiation therapy, in vivo treatment of tumors (MC38 or Panc02-SIY) avoided tumor-draining lymph nodes. Flow cytometry gates (FIG. 2B) identified DC1 infiltrating the tumor. CCR7 expression (FIG. 2C) showed that the DC1 population of dendritic cells failed to mature in Panc02-SIY tumors treated with a range of radiation doses.

Example 3

Identification of Differentially Regulated Genes by scRNASeq

Dendritic cells differentially mature in the two tumors types. To distinguish these tumor types, infiltrating cells from MC38 and Panc02-SIY tumors were isolated and single cell sequencing was performed. Differentially regulated genes were enriched in MC38 DC versus Panc02-SIY DC. Analyzing four replicate tumors (untreated vs. treated with radiation therapy) CD45+ cells were sorted and processed for scRNASeq. using a 10× Genomics device. Cross-presenting dendritic cells were identified by gene expression, including the characteristic gene Zbtb46 and Batf3 (FIG. 3A). Cells were clustered based on gene expression profiles to generate tSNE plots, and dendritic cells were identified based on expression of characteristic genes. Genes that were enriched in MC38 DC versus Panc02-SIY DC were calculated. Comparative analysis of enriched genes in dendritic cells in Panc02-SIY tumors showed that DNAse1L3 was 3.8-fold enriched in Panc02-SIY dendritic cells (p=0.002) (FIG. 3B).

Example 4

In Vitro DNAse1L3 Inhibition Stimulates DC Maturation

Figure 4:
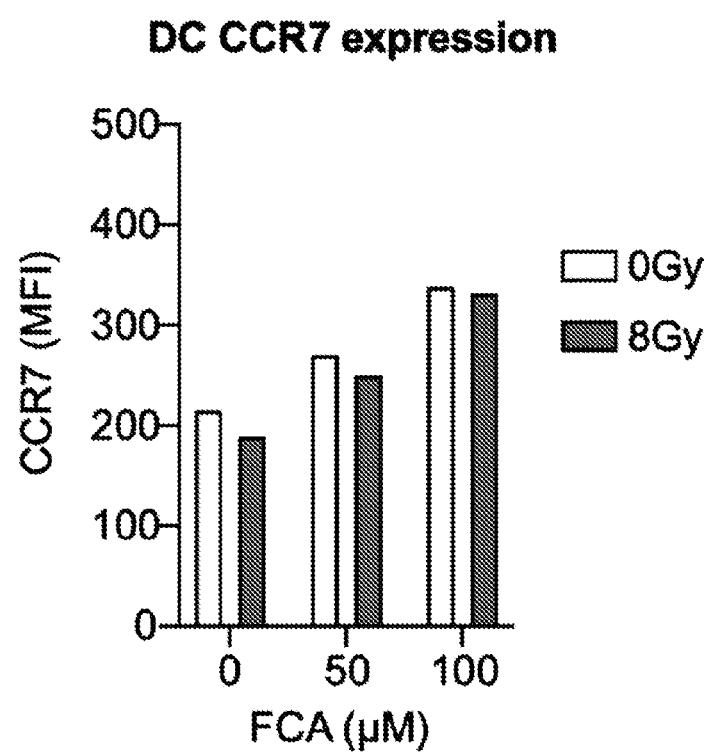
FIG. 4 depicts CCR7 expression in DCs that were cultured with cancer cells, where the cancer cells were untreated (0Gy) or irradiated (8Gy). These co-cultures were treated with 0, 50, or 100 micromolar Fmoc-d-cyclohexyl-alanine (FCA) to inhibit DNAse1L3.

This example shows that inhibition of DNAse1L3 stimulates DC maturation when cultured with untreated or irradiated cancer cells. Dendritic cells were cultured (with untreated or irradiated cancer cells) and treated with increasing doses of FCA, an inhibitor of DNAse1L3 (FIG. 4). Cancer cells were co-cultured with dendritic cells and were treated with 0, 50, or 100 micromolar Fmoc-d-cyclohexyl-alanine (FCA) to inhibit DNAse1L3.

DNAse1L3 inhibition resulted in a significant increase in dendritic cell maturation as assessed by the upregulation of markers including CCR7, a molecule that is key for dendritic cell migration to draining lymph nodes and cross-presentation to CD8 T cells located in draining lymph nodes. CCR7 expression on DCs was assessed by flow cytometry 24 hours after culturing.

Example 5

DNAse1L3 Regulation of Tumor Immune Responses

Figure 5A:
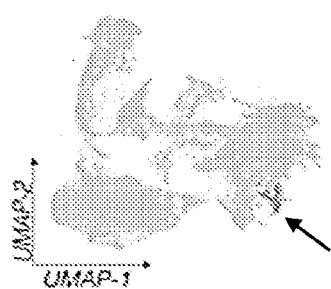
FIGS. 5A-5D show that increased DNAse1L3 expression correlates with decreased nucleic acid sensing in P2SIY tumors. MC38 or P2SIY tumor bearing mice were treated with 12Gy radiation (RT) or left untreated (NT). 24 hours post treatment, sorted tumor CD45+ cells were processed for scRNAseq. cDCs were identified by graph-based clustering and Zbtb46 expression (arrow) (FIG. 2A).
Figure 5B:
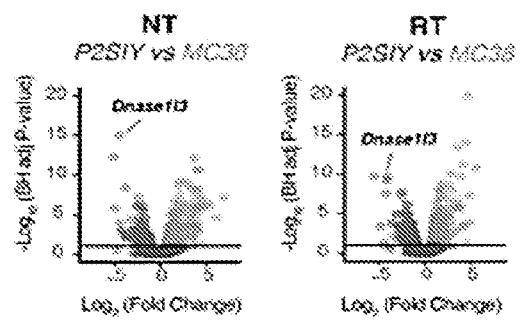
Figure 5C:
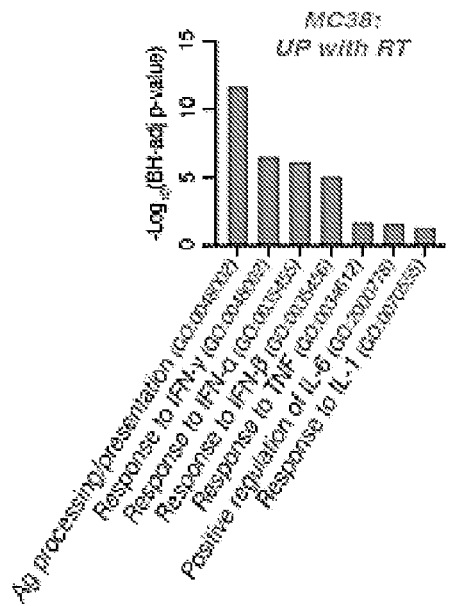
Figure 5D:
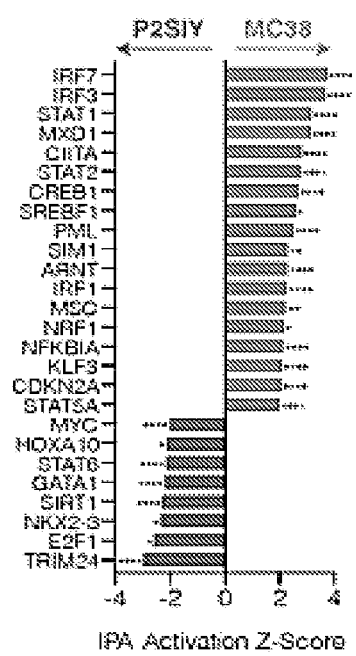

In tumors where DCs fail to mature following radiation therapy, DNAse1L3 was upregulated in the tumor DC (FIG. 5A). In these poorly radioimmunogenic tumors, DCs do not efficiently traffic to the tumor-draining lymph node and fail to establish a CD8 T cell response that can help control residual disease following radiation therapy. Pathway analysis of the genes differentially regulated in radioimmunogenic versus poorly radioimmunogenic tumors demonstrated that a range of inflammatory pathways related to DNA and RNA sensing failed in the poorly radioimmunogenic tumors (FIGS. 5B-5D). These results suggest that DNAse1L3 upregulation is a potential mechanistic explanation for the failure in nucleic acid sensing between two tumors in otherwise genetically identical mice.

Example 6

Conditional DNAse1L3 Knockout Mice

Figure 6A:
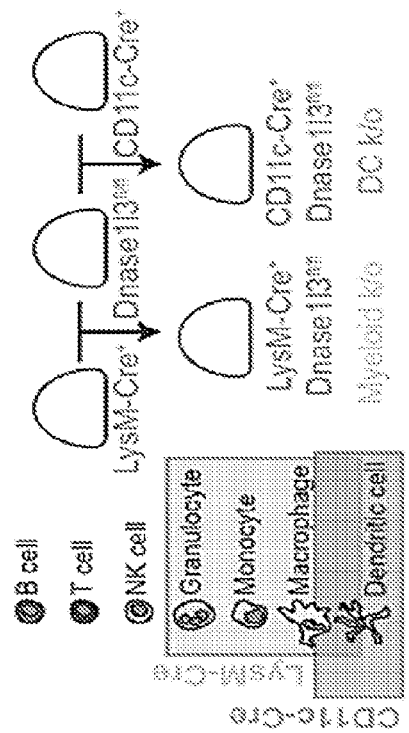
FIGS. 6A-6C depict results in conditional DNAse1L3 knockout mice.
Figure 6B:
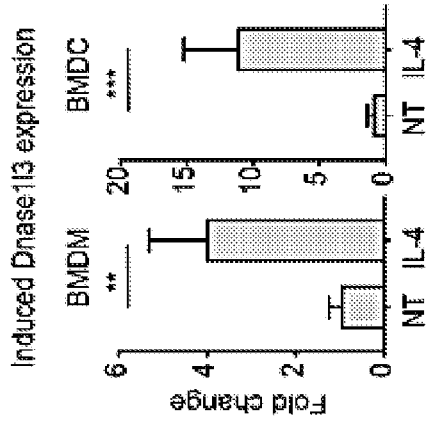
Figure 6C:
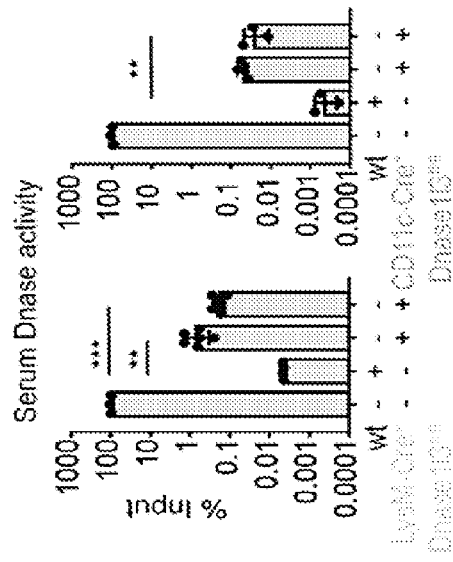

Initial experiments demonstrated that DNAse1L3 is upregulated in macrophages by M2 differentiation stimuli (FIG. 6A). Mice with conditional knockouts of DNAse1L3 in myeloid cells and dendritic cells were constructed as shown in FIG. 6B. In mice lacking DNAse1L3 in myeloid cells (LysM-Cre DNAse1l3$^{fl/fl}$ mice), mouse serum showed a 2 log-fold decrease in its ability to degrade polynucleosomes (FIG. 6C), indicating myeloid cells are an important source of this activity. Similarly, where loss of DNAse1L3 was restricted to dendritic cells (CD11c-Cre DNAse1l3$^{fl/fl}$ mice), mouse serum also showed a 2 log-fold decrease in the ability to degrade polynucleosomes (FIG. 6C). These data suggest that macrophages and dendritic cells can construct a zone of DNA degradation, with the potential to limit the ability of microvesicles to provide innate adjuvant signals.

Figure 7E:
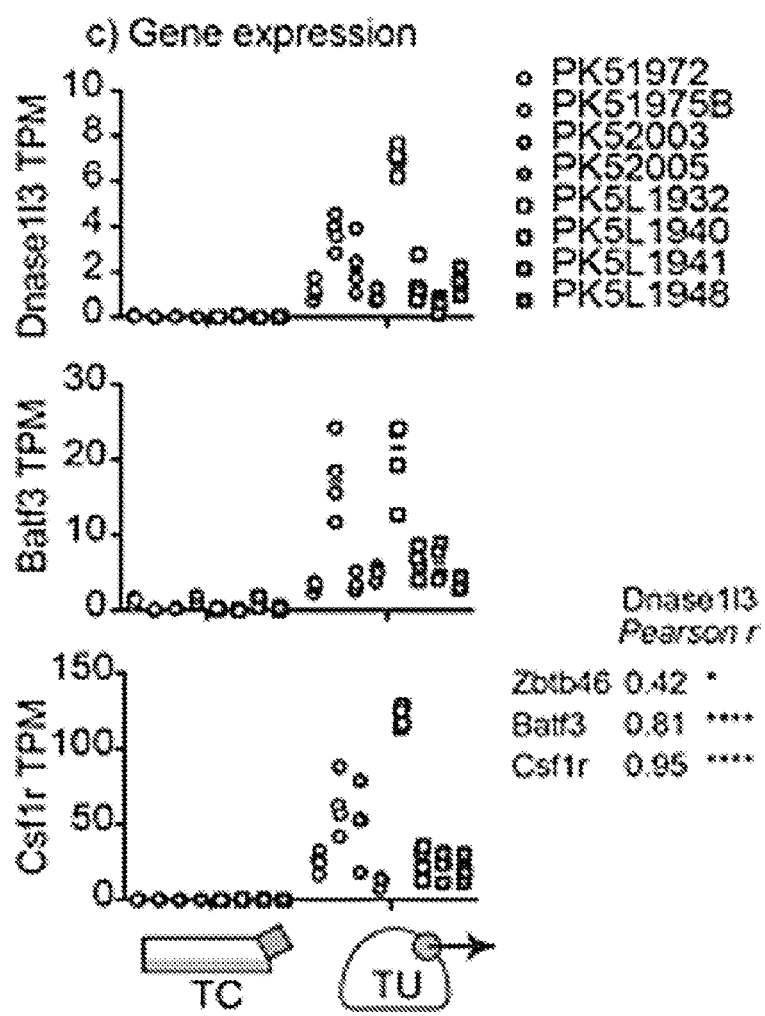

To model cancer in these mice, a series of pancreatic cancer cell lines from Pdx-Cre$^{+/-}$ Kras$^{(G12D)+/-}$ Trp53$^{(R172H)+/-}$ mice and another set from a further cross-breeding with Luciferase-SIY$^{fl/fl}$ were developed to permit both bioluminescent targeting and an integrated model antigen (FIG. 7A). These cell lines cover a range of grades and have abundant myeloid infiltration (FIG. 7B). Importantly, these tumors vary in their in vivo expression of DNAse1L3, and expression of DNAse1L3 has a good correlation to myeloid infiltration (FIG. 7C). At present, a panel of cell lines derived from genetically relevant spontaneous tumors represent the best possible model to rapidly test novel therapies in complicated genetic knockouts where existing Cre-mediated gene regulation means that spontaneous tumors are not feasible. Moreover, the subset of cell lines bearing a model antigen provides a shared antigenic target between the models that are otherwise antigenically disparate and neoantigen poor—a limitation of genetically regulated spontaneous models.

Example 7

Effect of Myeloid Expression of DNAse1L3 on Immune Response to Radiation

Experiments to determine the consequence of myeloid expression of DNAse1L3 on the immune response to radiation therapy are performed. Tumors are established and treated in mice with conditional deletions of DNAse1L3 and the effect of DNAse1L3 loss on survival following treatment is determined. Further, the effect of treatment on tumor-specific T cell responses, the importance of such responses in local control, and the impact of DNAse1L3 on systemic anti-tumor immunity resulting from treatment are measured.

Tumors are established and treated in mice with conditional deletions of DNAse1L3 (See Example 6). Initial experiments use the single high dose of 12Gy, where DNAse1L3 is associated with differential nucleic acid signaling. This can be altered to a fractionated regimen with matched BED if additional preclinical studies are warranted based on initial results. A panel of Pdx-Cre$^{+/-}$ Kras$^{(G12D)+/-}$ Trp53$^{(R172H)+/-}$ and Luciferase-SIY$^{fl/fl}$ pancreatic tumors are tested in wild-type (or DNAse1l3$^{fl/fl}$ littermate controls), LysM-Cre DNAse1l3$^{fl/fl}$, and CD11cCre DNAse1l3$^{fl/fl}$ mice. These mice are treated with 12Gy focal RT and followed for tumor growth rate and survival following treatment.

Further, to understand how selective loss of DNAselL3 impacts the tumor immune environment, experiments flow cytometry is used to identify infiltrating T cell and myeloid subsets in the tumor. Changes in tumor-specific T cells in the tumor following treatment, and in myeloid populations that might be impacted by selective DNAse1L3 loss are assessed using flow cytometry. Wild-type, LysM-Cre DNAse1L3$^{fl/fl}$, and CD11cCre DNAse1L3$^{fl/fl}$ mice bearing d14 PK5L1940 tumors are treated with 12Gy focal radiation and harvested 3 and 7 days following treatment. A single cell suspension is prepared by dissection into 2 mm fragments followed by agitation in digest solution. The digest is filtered through 100 μm nylon mesh to remove macroscopic debris and cells are stained with antibodies to CD3, CD4, FoxP3, CD8, CD25, CD69, CD103, CD39, CD62L, CD44, CD127, and Ly6C, along with the SIY-pentamer to identify SIY-specific CD8 T cells. This panel allows for identification of Treg (CD4$^+$CD25$^+$FoxP3$^+$), TRM (CD8$^+$CD69$^+$CD103$^+$CD39$^+$), CD8 effectors (CD8$^+$CD44$^+$CD62L$^-$CD127$^-$) tumor-specific T cells (SIY-MHCpentamer$^+$ in addition to the former markers), and CD4 effectors (CD4$^+$CD44$^+$FoxP3$^-$CD62L$^-$CD127$^-$Ly6C$^+$). In addition, a second panel of antibodies to myeloid markers is used, including CD11b, MHCII, Gr1, Ly6C, Ly6G, CD11c, CD24, CD103, F4/80, CCR7, CD80 and PDL1, to distinguish CD11b$^+$Gr1$^{hi}$Ly6C$^{int}$MHCII$^-$F4/80$^-$ granulocytes, CD11b$^+$Gr1$^{int}$Ly6C$^{hi}$MHCII$^-$F4/80$^-$ monocytes, CD11b$^+$Ly6C$^-$MHCII$^+$Gr1$^{low}$F4/80$^+$ TAM, Ly6C$^-$MHCII$^+$F4/80$^-$CD24$^+$CD11b$^-$CD103$^+$CD103$^+$DC (DC1), and Ly6C$^-$MHCII$^+$F4/80$^-$CD24$^+$CD11b$^+$CD103$^-$CD11b$^+$DC (DC2). The DCs are also tested for their maturation status by assessing expression of CCR7, CD80 and PDL1. These data provide an initial overview of the effect of selective DNAse1L3 loss on major immune populations infiltrating the tumors following radiation therapy.

To assess whether conditional deletion of DNAse1L3 restores DC migration to the TDLN following radiation therapy, tumor draining lymph nodes are harvested from the mice at d3 and d7 as above. Single cell suspensions of lymph node cells are prepared using a mild enzymatic digestion to allow full analysis of DC populations in the lymph nodes. Migratory and resident DCs are profiled in the TDLN using quantitative flow cytometry, including maturation markers such as CD40, CD80, and CD86 to determine whether selective loss of DNAse1L3 restores the number and maturation phenotype of dendritic cells following radiation therapy.

In addition to the tumor and lymph node studies above, the effect of selective DNAse1L3 loss on systemic tumor-specific immunity is evaluated by tracking SIY-specific T cells. In mice with tumors expressing SIY, peripheral blood is harvested every two weeks following tumor implantation starting at d7, at which time circulating tumor-specific T cells are first detected in mice. The second collection time point (d21) occurs 7 days following radiation therapy (d14), at which time restoration of circulating immunity following radiation therapy and immunotherapy has been shown, and which otherwise declines below detection in untreated mice. Quantitative flow cytometry of whole peripheral blood is used to count SIY-specific T cells in the circulation over time. To determine whether this T cell response is mechanistic, models are selected wherein DNAse1L3 loss effects the response to radiation therapy. Studies are repeated with CD4 or CD8 T cell depletion starting 1 day prior to radiation therapy. To determine whether local therapy impacts distant tumors, tumors are simultaneously established in both flanks to avoid the immunogenicity of a delayed second tumor model, and one tumor is treated with radiation as above. The response of the out of field tumor is monitored. These experiments formally demonstrate that conditional loss of DNAse1L3 impacts tumor control in poorly radioimmunogenic pancreatic tumor models, as well.

Example 8

Effect of Myeloid Expression of DNAse1L3 on Tumor Immune Environment Response to Radiation Therapy The immune environment of tumors in mice with conditional deletions of DNAse1L3 is characterized, and evidence of changed nucleic acid signaling in the tumor is examined. In addition, a model is developed to understand regulation of DNAse1L3 in the tumor environment.

This Example uses unbiased approaches to characterize the immune environment of tumors in mice with conditional deletions of DNAse1L3 and evidence of changed nucleic acid signaling in the tumor. While the immune environment of tumors following radiation therapy has been characterized generally, the effect of selective DNAse1L3 loss remains to be determined. However, it is possible that broad cell populations do not change, such as with Mertk$^{-/-}$ and myeloid selective Myd88$^{-/-}$ despite dramatic effects on outcomes. However, in these examples, changes in cytokine and chemokine patterns in tumors were detected as a result of changed differentiation of myeloid cells in the tumors. It is predicted that selective loss of DNAse1L3 will produce similar outcomes. For this reason, transcriptional changes in the tumor immune environment are assessed to identify evidence of altered nucleic acid signaling and to identify any unexpected responses. Finally, regulation of DNAse1L3 in tumors is analyzed to explain the dramatic variability between models.

To transcriptionally analyze tumors selectively lacking DNAse1L3, a representative tumor that responsive to selective loss of DNAse1L3 is selected. Wild-type, LysM-Cre DNAse1l3$^{fl/fl}$, and CD11cCre DNAse1l3$^{fl/fl}$ mice bearing d14 PK5L1932 tumors are untreated or treated with 12Gy focal radiation. Three and seven days later, tumors are harvested (n=4 animals/group) and banked into RNALater preservation buffer. RNA purification is performed using a Qiagen RNeasy Micro purification kit, and RNA-seq libraries are prepared using the SMART-Seq Ultra Low Input RNA kit. Samples are multiplexed and sequenced at 50 million reads per sample on an Illumina NovaSeq 6000 instrument. Briefly, after conversion to fastq, RNA-seq reads are mapped and quantified at the gene level using the Salmon analysis package, and pairwise group differences are assessed using Voom/Limma in R and Bioconductor. Differential transcript usage per gene is also assessed using Salmon/DEXseq, and novel transcript isoform detection is performed using GESS and MISO. Differences are also assessed at the functional pathway level and for conserved transcription factor binding motifs mined from ENCODE datasets using Enrichr. In addition, Ingenuity Pathway Analysis software (Qiagen) is used to identify potential regulators and pathways that explain the differential gene expression pathways. This approach identifies the transcription factors responsible for distinct gene expression in the presence or absence of DNAse1L3, while functional analysis at the gene and pathway level identifies additional pathways and molecules that may explain any changed outcome in treated tumors. In particular, RNA profiles are examined for transcriptional signatures associated with nucleic acid signaling and gene induction associated with exposure to type I IFN. These experiments identify the transcriptional regulation that results in differential activation following selective loss of DNAse1L3 in these tumors.

To map these transcriptional signatures to specific cell types, scRNASeq is performed using treated tumors. A single cell suspension of treated tumors is prepared and CD45+ cells are flow sorted for further analysis. Tumors are harvested at either d3 or d7 as determined by total RNASeq above, processed into a single cell suspension and magnetically enriched using CD45 MicroBeads (Miltenyi Biotec). Enriched cells are labeled with viability dye and CD45-APC. Live CD45$^+$ cells are sorted to high purity using a 1 cell sorter and cells are processed. Libraries are sequenced. Data are processed using the Cell Ranger pipeline (v3.1) and subsequently analyzed with the Loupe Browser from 10× Genomic (v5.0). Significantly altered transcripts are mapped to populations generated by automated graph-based clustering or hand-curated marker genes of known immune subsets. These experiments identify the cell types responsible for novel gene processes regulated on conditional loss of DNAse1L3 in tumors. In further experiments, a comprehensive cloud-based integration of RNAseq, IHC, and clinical data from patients with pancreatic cancer is gathered. Initial analyses are focused on immune infiltrates and outcome. In the present Example, statistical associations with expression of target genes of interest, including DNAse1L3, are identified and enrichment analyses of these associations are performed, with a particular focus on interferon signaling and Notch signaling according to published mechanisms of DNAse1L3 regulation. Additionally, multivariate and machine learning regression (continuous target variables) and classification (categorical/cohort target variables) models are developed that predict expression of target genes or clinical features of interest, and these are compared to univariate approaches. As these models are developed and evaluated, an independent data set is compiled from additional patients for the purposes of model validation. Co-regulated genes are identified that may explain high expression of DNAse1L3 in some tumors that results in poor immunity.

Example 9

Methods of Treating a Subject with Cancer

This Example describes methods of treating a subject with a cancer using an inhibitor of DNAse1L3 and an effective amount of radiation. In this Example, treatment enhances or induces the response of tumor-associated immune cells in the subject. However, one skilled in the art will appreciate that methods that deviate from these specific methods can also be used to successfully treat or inhibit a cancer in a subject.

The subject is treated with an inhibitor of DNAse1L3, such as a small molecule, an antibody, an antibody fragment, a DNAse1L3 aptamer, an inhibitory RNA, or a combination of two or more thereof. For example, the subject is treated with Fmoc-d-cyclohexylalanine (FCA), DR396, PV6R, or heparin. One or more immune-modulatory molecules, one or more additional anti-cancer agents, and/or one or more adjuvants, antigens, vaccines, allergens, antibiotics, gene therapy vectors, vaccines, kinase inhibitors, MerTK inhibitors, co-stimulatory molecules, TLR agonists, or TLR antagonists may also be administered to the subject. Radiation therapy is administered locally to the tumor. The response of the subject's tumor is monitored, such as for up to 5 years or for more than 5 years.

Example 10

Methods of Selecting and Treating a Subject with Cancer

This Example describes methods of selecting and treating a subject with a cancer using an inhibitor of DNAse1L3 and an effective amount of radiation. In this Example, a subject with increased DNAse1L3 is selected for treatment with an inhibitor of DNAse1L3 and radiation. However, one skilled in the art will appreciate that methods that deviate from these specific methods can also be used to successfully treat or inhibit a cancer in a subject.

A tumor or blood sample is collected from a subject with a cancer, for example pancreatic adenocarcinoma or colorectal adenocarcinoma. The amount of DNAse1L3 in the sample, such as in macrophages or dendritic cells of the sample, is measured, such as by detecting DNAse1L3 nucleic acids or proteins in the sample. If an increased amount of DNAse1L3 in the sample compared to a control is determined, the subject is selected for treatment with an inhibitor of DNAse1L3 and radiation therapies.

The subject is treated with an inhibitor of DNAse1L3, such as a small molecule, an antibody, an antibody fragment, a DNAse1L3 aptamer, an inhibitory RNA, or a combination of two or more thereof. For example, the subject is treated with Fmoc-d-cyclohexylalanine (FCA), DR396, PV6R, or heparin. One or more immune-modulatory molecules, one or more additional anti-cancer agents, and/or one or more adjuvants, antigens, vaccines, allergens, antibiotics, gene therapy vectors, vaccines, kinase inhibitors, MerTK inhibitors, co-stimulatory molecules, TLR agonists, or TLR antagonists may also be administered to the subject. Radiation therapy is administered locally to the tumor. The response of the subject's tumor is monitored, such as for up to 5 years or for more than 5 years.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for treating a subject with pancreatic carcinoma or colorectal adenocarcinoma, comprising:
   Administering to the subject at least one dose of an effective amount of radiation therapy; and administering to the subject at least one dose of an effective amount of a small molecule inhibitor of DNAse1L3, wherein the small molecule inhibitor of DNAse1L3 is administered to the subject systematically and wherein the small molecule inhibitor is Fmoc-d-cyclohexylalanine (FCA), and wherein the radiation therapy and the inhibitor of DNAse1L3 are administered in either order.

2. The method of claim 1, wherein the radiation therapy is administered locally to the tumor.

3. The method of claim 1, wherein the radiation therapy is administered before the inhibitor of DNAse1L3.

4. The method of claim 1, further comprising administering to the subject one or more immune-modulatory molecules.

5. The method of claim 4, wherein the immune-modulatory molecules target PD-1, PD-L1 (B7-H1), CTLA-4, or LAG3.

6. The method of claim 1, wherein the inhibitor of DNAse1L3 stimulates tumor-associated dendritic cell maturation.

7. The method of claim 1, further comprising administering to the subject a second anti-cancer therapeutic agent.

8. The method of claim 1, wherein the systemic administration is intravenous administration.

9. A method for treating a subject with pancreatic cancer or colorectal adenocarcinoma by enhancing or inducing response of tumor-associated immune cells in the subject, comprising:
   administering to the subject an effective amount of radiation therapy; and
   administering to the subject an effective amount of a small molecule inhibitor of DNAse1L3, wherein the small molecule inhibitor of DNAse1L3 is administered to the subject systemically and wherein the small molecule inhibitor is Fmoc-d-cyclohexylalanine (FCA),
   thereby enhancing or inducing the response of tumor-associated immune cells in the subject.

10. The method of claim 9, wherein the tumor-associated immune cells comprise dendritic cells or macrophages.

11. The method of claim 9, wherein the systemic administration is intravenous administration.

12. A method of treating a subject with a pancreatic adenocarcinoma tumor or a colorectal adenocarcinoma tumor, comprising:
   measuring an amount of DNAse1L3 in macrophages, dendritic cells, a tumor sample, or a blood sample from the subject;

determining an increased amount of DNAse1L3 in macrophages, dendritic cells, tumor sample, or blood sample compared to a control; and treating the subject, comprising:
- administering to the subject an effective amount of radiation therapy; and
- administering to the subject an effective amount of a small molecule inhibitor of DNAse1L3, wherein the small molecule inhibitor of DNAse1L3 is administered to the subject systemically and wherein the small molecule inhibitor is Fmoc-d-cyclohexylalanine (FCA).

13. The method of claim 12, wherein measuring the amount of DNAse1L3 comprises detecting DNAse1L3 nucleic acids or proteins in the dendritic cells or tumor sample.

14. The method of claim 12, wherein the systemic administration is intravenous administration.

* * * * *

SEQUENCE LISTING

<160> NUMBER OF SEQ ID NOS: 2

<210> SEQ ID NO 1
<211> LENGTH: 1414
<212> TYPE: DNA
<213> ORGANISM: Homo sapiens

<400> SEQUENCE: 1

```
gccagaatcc agcactccaa gcactgctgt cttctcacag agtcttgaag ccagagcagc    60
gccaggatgt cacgggagct ggccccactg ctgcttctcc tcctctccat ccacagcgcc   120
ctggccatga ggatctgctc cttcaacgtc aggtcctttg gggaaagcaa gcaggaagac   180
aagaatgcca tggatgtcat tgtgaaggtc atcaaacgct gtgacatcat actcgtgatg   240
gaaatcaagg acagcaacaa caggatctgc cccatactga tggagaagct gaacagaaat   300
tcaaggagag gcataacgta caactatgtg attagctctc ggcttggaag aaacacatat   360
aaagaacaat atgcctttct ctacaaggaa aagctggtgt ctgtgaagag gagttatcac   420
taccatgact atcaggatgg agacgcagat gtgttttcca gggagccctt tgtggtctgg   480
ttccaatctc cccacactgc tgtcaaagac ttcgtgatta tcccctgca caccacccca   540
gagacatccg ttaaggagat cgatgagttg gttgaggtct acacggacgt gaaacaccgc   600
tggaaggcgg agaatttcat tttcatgggt gacttcaatg ccggctgcag ctacgtcccc   660
aagaaggcct ggaagaacat ccgcttgagg actgacccca ggtttgtttg gctgatcggg   720
gaccaagagg acaccacggt gaagaagagc accaactgtg catatgacag gattgtgctt   780
agaggacaag aaatcgtcag ttctgttgtt cccaagtcaa acagtgtttt tgacttccag   840
aaagcttaca gctgactga agaggaggcc tggatgtca cgaccactt tccagttgaa   900
tttaaactac agtcttcaag ggccttcacc aacagcaaaa aatctgtcac tctaaggaag   960
aaaacaaaga gcaaacgctc ctagacccaa gggtctcatc ttattaacca tttcttgcct  1020
ctaaataaaa tgtctctaac agatatgaac tgctccctgt acttaggaaa caagagtgat  1080
ccaactgctt tcattttttg acctgaattt attctgactt gagccaaatt ggaaggagaa  1140
tcttttgtat ctctcttggt tcatacctc ccctgaattg tctaaaaggg aaccagggge  1200
atttgtagac caaatgatg atcttcatgc cctgagccag agcccatcc actgtcactg   1260
gccctgctca accctgtcat gcgagaggct gcaggggag gaagagcgtc agctttcagt  1320
cctcatgagg ggtcctgttc cacacgcaat gaccagaaac accaaggccc cagctgcccc  1380
tgtgatttgg gcaattaact gttttaagag tctg                             1414
```

<210> SEQ ID NO 2
<211> LENGTH: 305
<212> TYPE: PRT
<213> ORGANISM: Homo sapiens

<400> SEQUENCE: 2

```
Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
```

```
                65                  70                  75                  80
Arg Gly Ile Thr Tyr Asn Tyr Val Ile Ser Ser Arg Leu Gly Arg Asn
                    85                  90                  95
Thr Tyr Lys Glu Gln Tyr Ala Phe Leu Tyr Lys Glu Lys Leu Val Ser
                100                 105                 110
Val Lys Arg Ser Tyr His Tyr His Asp Tyr Gln Asp Gly Asp Ala Asp
                115                 120                 125
Val Phe Ser Arg Glu Pro Phe Val Val Trp Phe Gln Ser Pro His Thr
    130                 135                 140
Ala Val Lys Asp Phe Val Ile Ile Pro Leu His Thr Thr Pro Glu Thr
145                 150                 155                 160
Ser Val Lys Glu Ile Asp Glu Leu Val Glu Val Tyr Thr Asp Val Lys
                165                 170                 175
His Arg Trp Lys Ala Glu Asn Phe Ile Phe Met Gly Asp Phe Asn Ala
                180                 185                 190
Gly Cys Ser Tyr Val Pro Lys Lys Ala Trp Lys Asn Ile Arg Leu Arg
                195                 200                 205
Thr Asp Pro Arg Phe Val Trp Leu Ile Gly Asp Gln Glu Asp Thr Thr
    210                 215                 220
Val Lys Lys Ser Thr Asn Cys Ala Tyr Asp Arg Ile Val Leu Arg Gly
225                 230                 235                 240
Gln Glu Ile Val Ser Ser Val Val Pro Lys Ser Asn Ser Val Phe Asp
                245                 250                 255
Phe Gln Lys Ala Tyr Lys Leu Thr Glu Glu Glu Ala Leu Asp Val Ser
                260                 265                 270
Asp His Phe Pro Val Glu Phe Lys Leu Gln Ser Ser Arg Ala Phe Thr
        275                 280                 285
Asn Ser Lys Lys Ser Val Thr Leu Arg Lys Lys Thr Lys Ser Lys Arg
    290                 295                 300
Ser
305
```